US010434197B2

(12) United States Patent
Fox et al.

(10) Patent No.: US 10,434,197 B2
(45) Date of Patent: Oct. 8, 2019

(54) TETRAZINE-TRANS-CYCLOOCTENE LIGATION FOR THE RAPID CONSTRUCTION OF RADIONUCLIDE LABELED PROBES

(75) Inventors: Joseph M. Fox, Landenberg, PA (US); Matthew Hassink, Wilmington, DE (US); Melissa Blackman, Waltham, MA (US); Zibo Li, Logan, UT (US); Peter S. Conti, Pasadena, CA (US); Ramajeyam Selvaraj, Newark, DE (US)

(73) Assignees: University of Delaware, Newark, DE (US); University of Southern California, Los Angeles, CA (US)

( * ) Notice: Subject to any disclaimer, the term of this patent is extended or adjusted under 35 U.S.C. 154(b) by 1491 days.

(21) Appl. No.: 13/811,568

(22) PCT Filed: Jul. 21, 2011

(86) PCT No.: PCT/US2011/044814
§ 371 (c)(1),
(2), (4) Date: Jun. 24, 2013

(87) PCT Pub. No.: WO2012/012612
PCT Pub. Date: Jan. 26, 2012

(65) Prior Publication Data
US 2013/0266512 A1    Oct. 10, 2013

Related U.S. Application Data

(60) Provisional application No. 61/367,174, filed on Jul. 23, 2010.

(51) Int. Cl.
*A61K 51/00* (2006.01)
*A61M 36/14* (2006.01)
*A61K 51/04* (2006.01)
*C07D 257/08* (2006.01)
*C07D 401/14* (2006.01)
*C07D 403/12* (2006.01)

(52) U.S. Cl.
CPC ........ *A61K 51/0497* (2013.01); *C07D 257/08* (2013.01); *C07D 401/14* (2013.01); *C07D 403/12* (2013.01)

(58) Field of Classification Search
CPC .............. A61K 51/0497; C07D 257/08; C07D 401/14; C07D 403/12
USPC ...................................................... 424/1.89
See application file for complete search history.

(56) References Cited

U.S. PATENT DOCUMENTS 4,053,528 A    10/1977  Thorpe
2009/0023916 A1  1/2009  Fox et al.

FOREIGN PATENT DOCUMENTS

CN        101723849 A       6/2010
WO    WO 2006067376 A2 *   6/2006
WO    WO 2010/051530 A2    5/2010

OTHER PUBLICATIONS

Blackman et al. JACS, 2008, 130, 13518-13519.*
Zhang et al. Curr. Top. Med. Chem. 2007, 7, 1817-1828.*
Search Report for Chinese Patent Appl. No. 201180041210.X filed Jul. 21, 2011.
Chinese First Office Action dated Jun. 5, 2014 for Appl. No. 201180041210.X.
Selvaraj, Ramajeyam, et al., Tetrazine-trans-cyclooctene ligation for the rapid construction of integrin $\alpha_v\beta_3$ targeted PET tracer based on a cyclic RGD peptide, Bioorganic & Medicinal Chemistry Letters, 21 (2011), pp. 5011-5014.
Taylor, Michael T. et al., Design and Synthesis of Highly Reactive Dienophiles for the tetrazine-trans-Cyclooctene Ligation, Journal of the American Chemical Society, 2011, 133, pp. 9646-9649.
Taylor, Michael T. et al., Design and Synthesis of Highly Reactive Dienophiles for the tetrazine-trans-Cyclooctene Ligation, Journal of the American Chemical Society, 2011, 133, May 20, 2011, supporting information, pp. S-5 and S-7.
European Office Action for Application No. 11 810 394.4-1462 dated Mar. 25, 2015.
Rossin et al., In Vivo Chemistry for Pretargeted Tumor Imaging in Live Mice, Angew. Chem. Int. Ed. 2010, vol. 49, pp. 3375-3378.
Xie, et al., Proline-Catalyzed Direct Inverse Electron Demand Diels-Alder Reactions of Ketones with 1,2,4,5-Tetrazines, American Chemical Society, 2008, vol. 10, No. 10, pp. 1923-1926.
Li et al., Tetrazine-trans-cyclooctene ligation for the rapid construction of $^{18}$F labeled probes, Chem. Commun., vol. 46, 2010, pp. 8043-8045.
Guhlke et al., (2-[$^{18}$F]Fluoropropionyl-(D)phe$^1$)-octreotide, a Potential Radiopharmaceutical for Quantitative Somatostatin Receptor Imaging with PET: Synthesis, Radiolabeling, In Vitro validation and Biodistribution in Mice, Nuclear Medicine and Biology, Elsevier, NY, US, vol. 21, No. 6, 1994, pp. 819-825.
Devaraj et al., Fast and Sensitive Pretargeted Labeling of Cancer Cells through a Tetrazine/trans-Cyclooctene Cycloaddition, Angew. Chem. Int. Ed., vol. 48, 2009, pp. 7013-7016.
Devaraj et al., Bioorthogonal Turn-On Probes for Imaging Small Molecules inside Living Cells, Angew. Chem. Int. Ed., vol. 49, 2010, pp. 2869-2872.
Cai et al., A Thiol-Reactive $^{18}$F-Labeling Agent, N-[2-(4-$^{18}$F-Fluorobenzamido)Ethyl]Maleimide, and Synthesis of RGD Peptide-Based Tracer for PET Imaging of $\alpha_v\beta_3$ Integrin Expression, The Journal of Nuclear Medicine, vol. , No. 7, 2006, pp. 1172-1180.

(Continued)

Primary Examiner — Michael G. Hartley
Assistant Examiner — Sean R Donohue
(74) Attorney, Agent, or Firm — RatnerPrestia

(57) ABSTRACT

A Diels-Alder adduct of a trans-cyclooctene with a tetrazine is provided, wherein the adduct bears a substituent labeled with a radionuclide. A method of producing a PET or other image of an organ in an animal or human includes forming the Diels-Alder adduct in the animal or human. Trans-cyclooctenes and tetrazines suitable for preparing the adducts are provided.

21 Claims, 3 Drawing Sheets

(56) References Cited

OTHER PUBLICATIONS

Blackman et al., Tetrazine Ligation: Fast Bioconjugation Based on Inverse-Electron-Demand Diels-Alder Reactivity, J. Am. Chem. Soc., vol. 130, 2008, pp. 13518-13519.
Royzen et al., A Photochemical Synthesis of Functionalized trans-Cyclooctenes Driven by Metal Complexation, J. Am. Chem. Soc., vol. 130, 2008, pp. 3760-3761.
Supplemental European Search Report dated Oct. 29, 2013, for application EP 11 81 0394.
Written Opinion of the Int'l Searching Authority dated Mar. 28, 2012 for International Appl. No. PCT/US2011/044814.
P.A. Schubiger et al., "PET Chemistry", Springer Berlin Heidelberg, Dec. 31, 2007.
Chinese Office Action for Application No. 201180041210.X dated Jan. 23, 2015.
Chinese Office Action for Application No. 201180041210.X dated Jul. 14, 2015.
English translation of Chinese Office Action for Application No. 201180041210.X dated Jul. 14, 2015.

\* cited by examiner

TETRAZINE-TRANS-CYCLOOCTENE LIGATION FOR THE RAPID CONSTRUCTION OF RADIONUCLIDE LABELED PROBES

This application is the National Stage filing of International Application No. PCT/US2011/044814, filed 21 Jul. 2011, and claims priority of U.S. provisional Application No. 61/367,174, filed 23 Jul. 2010, the entireties of which applications are incorporated herein by reference for all purposes.

BACKGROUND OF THE INVENTION

Positron emission tomography (PET) is a non-invasive imaging modality that utilizes positron-emitting radionuclides (C-11, N-13, O-15 and F-18). For example, F-18 PET has a number of attributes that make it clinically attractive, including 100% positron efficiency, a very high specific radioactivity, and a short half-life of ~110 min. However, the short half-life of F-18 and the poor nucleophilicity of fluoride render it difficult to incorporate F-18 in complex molecules. Currently, radiochemistry is a major limiting factor for the field of PET. Despite recent advances, challenges exist for improving F-18 incorporation with respect to reaction rates, efficiency, and selectivity.

The inventors have previously described tetrazine-trans-cyclooctene ligation ('ITCO ligation') as a method of bioconjugation that proceeds with fast reaction rates without need for catalysis (M. L. Blackman, M. Royzen and J. M. Fox, *J. Am. Chem. Soc.* 2008, 130, 13518-13519) trans-Cyclooctene derivatives are readily prepared from cis-cyclooctenes using a photochemical flow-reaction that the inventors developed (M. Royzen, G. P. A. Yap and J. M. Fox, *J. Am. Chem. Soc.* 2008, 130, 3760-3761). The inventors have found that 3,6-diaryl-s-tetrazines offer an excellent combination of fast reactivity and stability for both the conjugate and starting material. In particular, 3,6-di(2-pyridyl)-s-tetrazines have been shown to display excellent characteristics. Thus, the reaction between trans-cyclooctene and 1a proceeds with a rapid rate ($k_2 \sim 2000$ M$^{-1}$ s$^{-1}$ in 9:1 MeOH:water), and is successful in cell media and cell lysate. 3,6-Di(2-pyridyl)-s-tetrazines can easily be functionalized as their amido derivatives (1b), which display excellent stability toward water and biological nucleophiles.

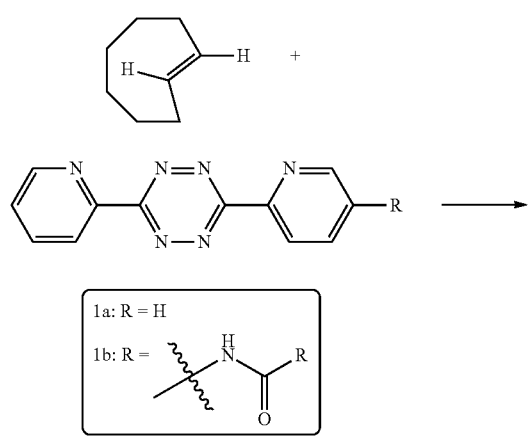

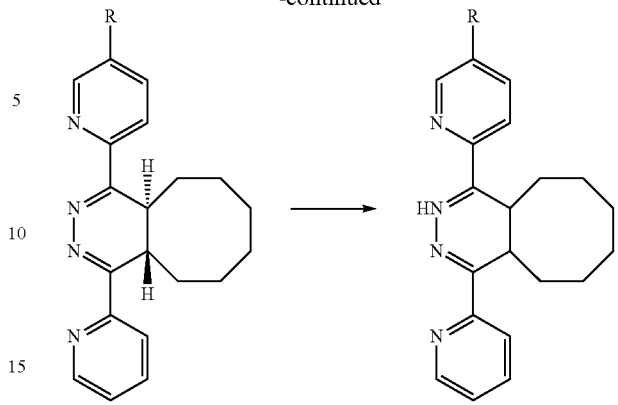

Because of the fast rate of reactivity, the TTCO-ligation offers opportunities for the rapid conjugation of radionuclides to biomolecules, both of which are often available only at low concentration.

SUMMARY OF THE INVENTION

In one aspect, the invention provides a Diels-Alder adduct of a trans-cyclooctene with a tetrazine, wherein the adduct bears a substituent labeled with a radionuclide.

In another aspect, the invention provides a method of producing a PET or other image of an organ in an animal or human. The method includes forming in the animal or human a Diels-Alder adduct of a trans-cyclooctene with a tetrazine, wherein the adduct bears a substituent labeled with a radionuclide.

In another aspect, the invention provides the compound according to structure 5

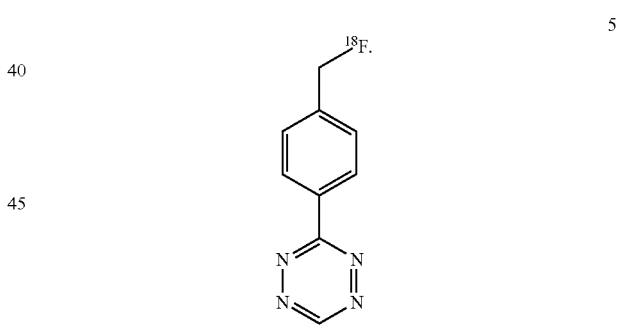

In another aspect, the invention provides the compound according to structure 9

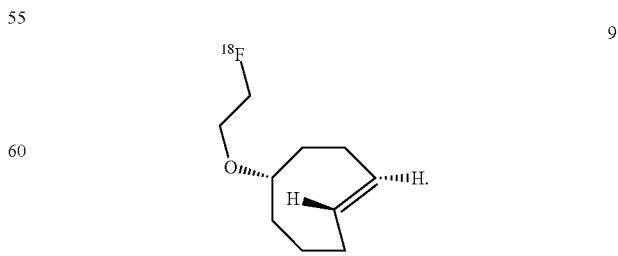

In another aspect, the invention provides the compound according to structure 17

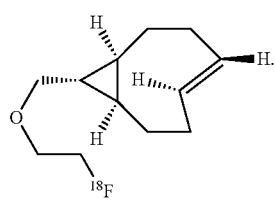

17

In another aspect, the invention provides the compound according to structure 13

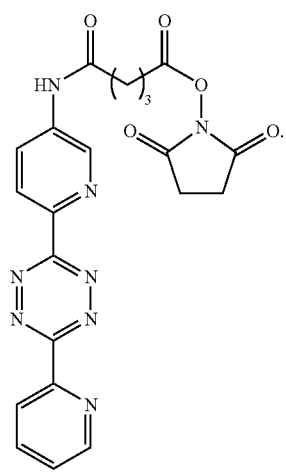

24

In another aspect, the invention provides the compound according to structure 24

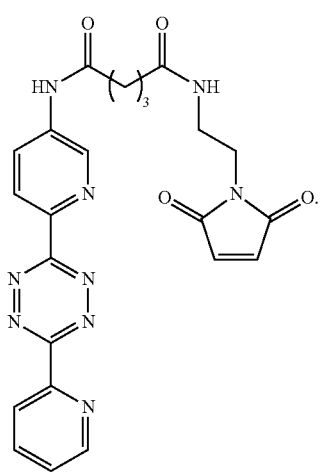

In another aspect, the invention provides the compound according to structure 25

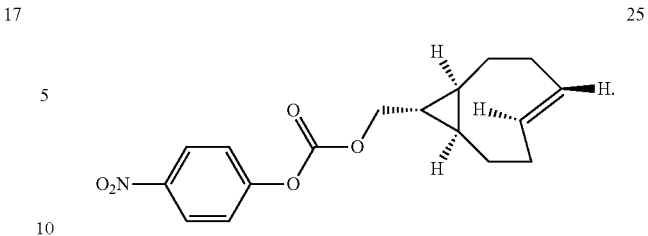

25

In another aspect, the invention provides the compound according to structure 26

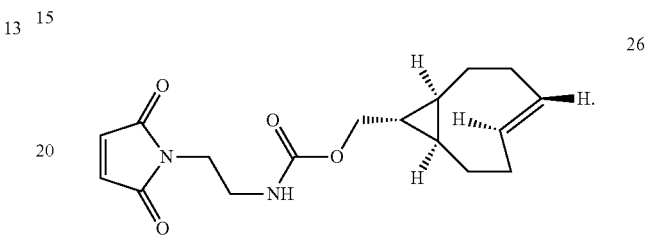

26

In another aspect, the invention provides the compound according to structure 27

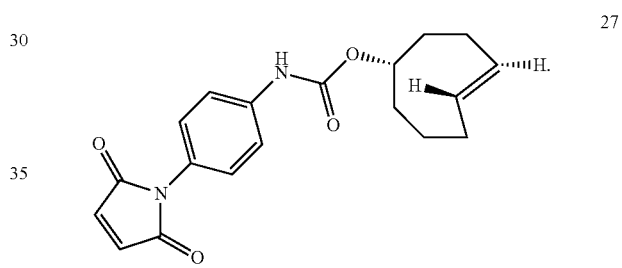

27

DETAILED DESCRIPTION OF THE INVENTION

Figure 1:
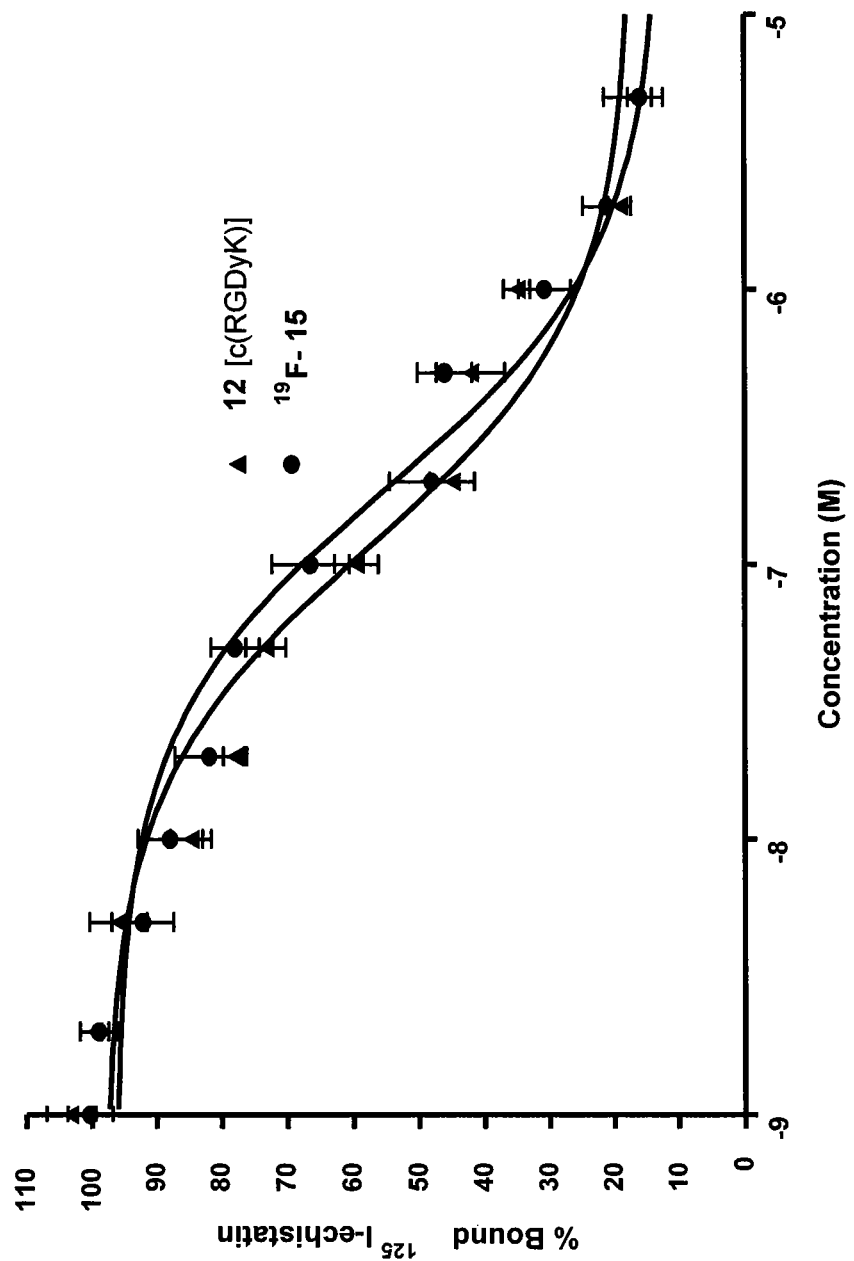
FIG. 1 shows cell binding affinity studies of c(RGDyK) (12) and $^{19}$F-15.

The invention provides an extremely fast and reactive method for generating radionuclide labeled probes based on TTCO-ligation, employing a Diels-Alder reaction between 3,6-diaryl-s-tetrazines and trans-cyclooctenes, one of which is labeled with a radionuclide, for example $^{18}$F. The reaction proceeds at exceptionally fast rates, providing effective conjugation method within seconds at low micromolar concentrations. Using the compounds and methods of the invention, it is possible to effectively label an organ in an animal or human for PET or other imaging. In a typical use, the Diels-Alder adduct is covalently bound to a biomolecule. This may be achieved via a linking group derived from a substituent present on the trans-cyclooctene or the tetrazine prior to reaction with the biomolecule.

The invention provides a number of ways to use TTCO-ligation for labeling, as will now be described. Labeling with $^{18}F$ will be described first, followed by a description of labeling with other radionuclides.

$^{18}F$-Labeled Tetrazines

The inventors focused on the development of direct methods for $^{18}F$-incorporation via reactions with fluoride ion, with an initial focus on the synthesis of $^{18}F$-labeled tetrazines (Scheme 1). Attempts to convert nitrotetrazine derivatives 2a and 2b into $^{18}F$-labeled substitution products 3 using $^{18}F$-fluoride/kryptofix or $^{18}F$-TBAF gave decomposition products and only traces of radiolabeled products. The inventors also combined mesylate 4 with fluoride, and in the most successful experiment ($^{18}F$-TBAF at 85° C. for 15 min) $^{18}F$-labeled product 5 was obtained in ~1% labeling yield.

Scheme 1. Synthesis of $^{18}F$-labeled tetrazines. Attepts to prepare 3 by nucleophilic substitution were low yielding. Fluorination of 4 ($^{18}F$-fluoride, MeCN, 85° C., 15 min) gave 5 in only 1% radiochemical yield.

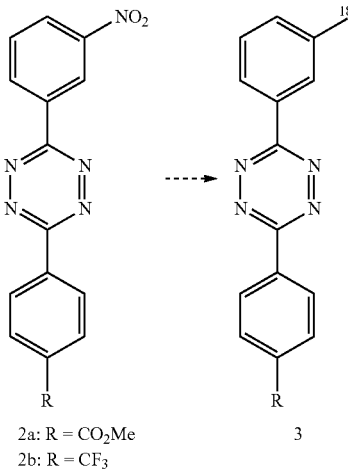

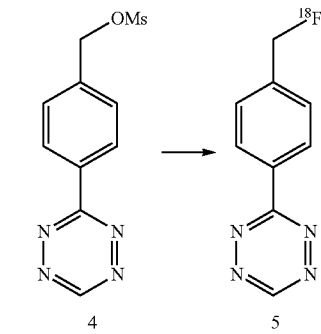

$^{18}F$-Labeled Trans-Cyclooctenes

The above difficulties prompted the inventors to consider methods for preparing $^{18}F$-labeled trans-cyclooctenes. To this end, the inventors synthesized the nosylate 8 as shown in Scheme 2. The key step in the synthesis was photoisomerization of 6 to 7 using a flow reactor that continuously removes the trans-isomers through selective metal complexation. See M. Royzen, G. Yap, and 3. Fox, *J. Am. Chem. Soc.* 2008, 130 (12), 3760. The major diastereomer of 7 was carried forward in the synthesis of 8.

Scheme 2. Synthesis of trans-cyclooctene nosylate 8. Reagents and conditions: (a) NaH, α-bromoacetic acid. (b) $CH_2N_2$, 69%, 2 steps (c) DIBAL, 78% (d) Methyl benzoate-sensitized photoisomerization with active removal of trans-isomers, $AgNO_3$, 55%. (e) NsCl, $Et_3N$, 87%.

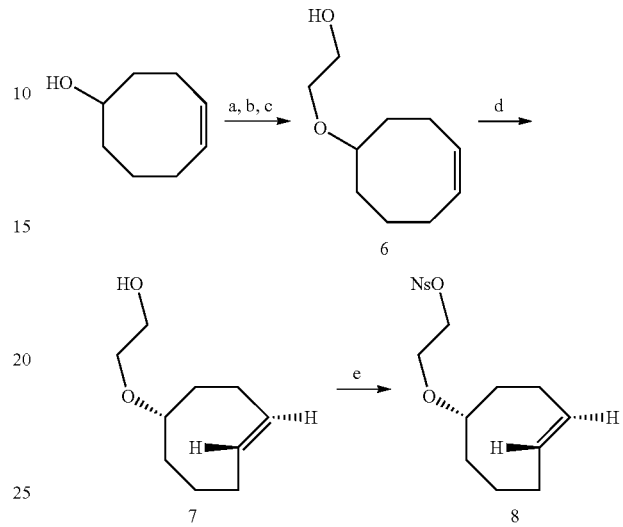

Nosylate 8 reacted efficiently with TBAF to provide $^{19}F$-9 in high yield. As used herein, the notation $^{19}F$— as part of a structure name indicates that the compound has not been radiolabeled, and $^{18}F$— indicates labeling.

Conditions for the preparation of $^{18}F$-9 were then optimized (Table 1). It was found that $^{18}F$-9 could be obtained in good yield by adding nosylate 8 to a mixture of [$^{18}F$]-fluoride fluoride (100 mCi)/tetrabutylammonium bicarbonate (TBAB) in acetonitrile (0.8 mL). The inventors determined the effect of varying the concentration of 8 in reactions conducted for 15 min at 75° C. (Table 1, entries 1-4).

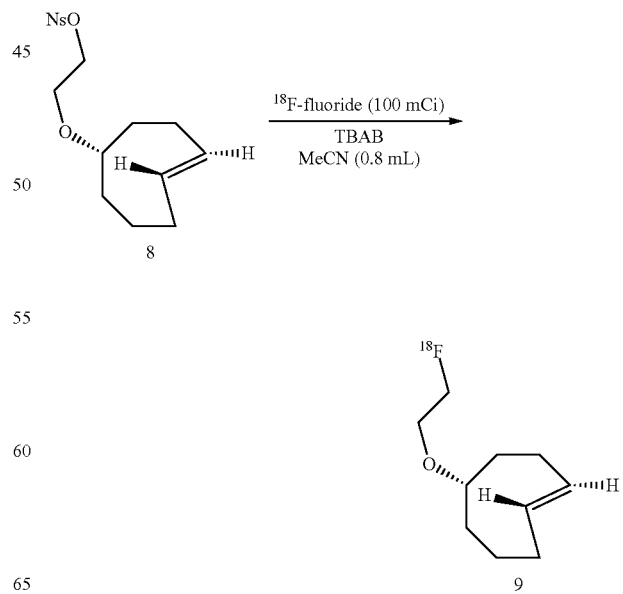

TABLE 1

Optimization of synthesis of $^{18}$F-labeled trans-cyclooctene

| Entry | Amount of 8 | Temp. | Reaction Time | Radiochemical Yield |
|---|---|---|---|---|
| 1 | 100 μg (0.35 mM) | 75° C. | 15 min | 18% |
| 2 | 500 μg (1.8 mM) | 75° C. | 15 min | 25% |
| 3 | 2.0 mg (7.0 mM) | 75° C. | 15 min | 71% |
| 4 | 3.0 mg (11 mM) | 75° C. | 15 min | 71% |
| 5 | 2.0 mg (7.0 mM) | 40° C. | 15 min | 24% |
| 6 | 2.0 mg (7.0 mM) | 55° C. | 15 min | 34% |
| 7[a] | 2.0 mg (7.0 mM) | 90° C. | 15 min | 71% |
| 8 | 2.0 mg (7.0 mM) | 75° C. | 3 min | 43% |
| 9 | 2.0 mg (7.0 mM) | 75° C. | 7 min | 68% |
| 10 | 2.0 mg (7.0 mM) | 75° C. | 30 min | 71% |

[a]Comparable results (70% radiochemical yield) were obtained under similar conditions using $K_2CO_3/K_{222}$ instead of TBAB.

The highest labeling yield (71%) was achieved with 7.0 mM 8, but a useful radiochemical yield (18%) was still obtained with 0.35 mM 8. Different reaction temperatures were studied, and 75° C. was found to be optimal (Table 1, entries 3, 5-7). Finally, the inventors investigated the efficiency of the $^{18}$F labeling as a function of time using 2 mg of 8 at 75° C. (Table 1, entries 8-10). While the labeling yield was optimal (71%) in an experiment conducted for 15 min, useful labeling yields were also obtained after 3 min (43%) and 7 min (68%). Overall, entry 3 appeared optimal for $^{18}$F labeling.

More generally, the invention provides analogs of $^{18}$F-9 in which the spacer group between O and $^{18}$F is an alkylene group. For example, the alkylene group may be a C2 alkylene group (as in $^{18}$F-9), or it may be any alkylene group from C3 to C20, more typically from C3 to C10, and most typically from C3 to C5. In another exemplary embodiment, an analog of $^{18}$F-9 uses an $^{18}$F—$CH_2$-phenyl moiety in place of the $^{18}$F—$CH_2$—$CH_2$ moiety of $^{18}$F-9. Such a compound may be prepared from the corresponding bromide, chloride, iodide, sulfonate, etc. by nucleophilic displacement with $^{18}$F fluoride.

The inventors also used a photochemical flow reactor (M. Royzen, G. Yap, and J. Fox, *J. Am. Chem. Soc.* 2008, 130 (12), 3760) to synthesize 16, an analog of 7 with a functionalizable group. The rate of the reaction of compound 16 with 3,6-di(2-pyridyl)-s-tetrazine (1a) in methanol was $k_2 = 22000$ M$^{-1}$s$^{-1}$, 18 times faster than the reaction of 1a with trans-cyclooctene in the same solvent. In aqueous solvent systems, reaction between 1a and 16 was even faster, in fact too fast to measure by UV-vis spectroscopy. (Tetrazine ligations show significant acceleration due to the hydrophobic effect.) In addition to excellent reactivity, 16 also displayed excellent stability, showing no degradation after 24 hours in water or human serum or when exposed to 5 mM n-butylamine in MeOH or to 5 mM ethanethiol in MeOH for 24 hours. Compound 16 can be readily converted into carbamate derivatives, and compound 16 can be selectively conjugated to the protein thioredoxin using the conjugation of maleimide 26 (vide infra) to a cysteine residue, and that conjugate can in turn can take part in tetrazine ligation analogous to that shown below for compound 16.

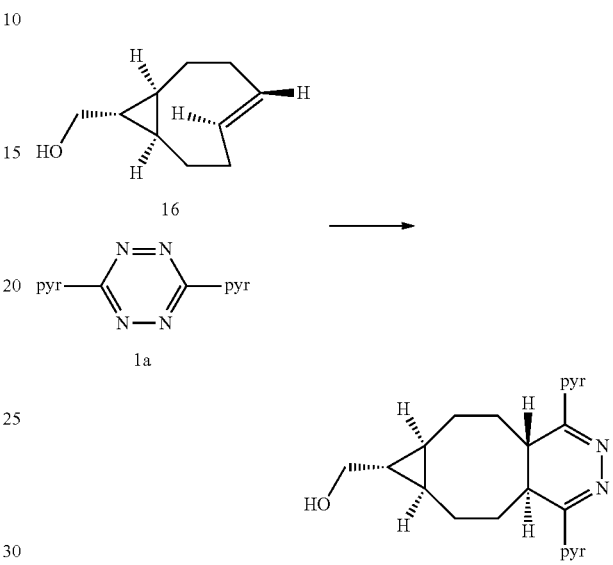

Labeled compound $^{18}$F-17 may be prepared from compound 16 using the same general procedures used for making labeled compound $^{18}$F-9.

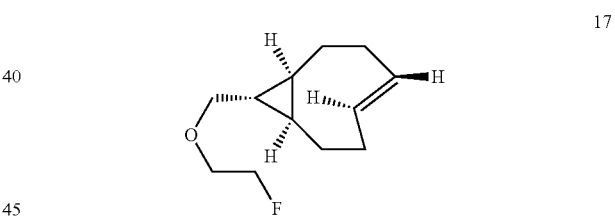

Reaction of $^{18}$F-Labeled Trans-Cyclooctenes with Tetrazines

Derivatives of 3,6-di(2-pyridyl)-s-tetrazine (e.g., 1b) are readily prepared by known methods, for example as described by M. L. Blackman, M. Royzen and J. M. Fox, *J. Am. Chem. Soc.* 2008, 130, 13518-13519 and R. Rossin, P. R. Verkerk, S. M. v. d. Bosch, R. C. M. Vulders, I. Verel, J. Lub and M. S. Robillard, *Angew. Chem. Int. Ed.* 2010, 49, 3375-3378. Therefore, 3,6-di(2-pyridyl)-s-tetrazine (1a) was used to test the efficiency of $^{18}$F-labeled trans-cyclooctene 9 in the TTCO-ligation. A 'cold' study with $^{19}$F-9 was initially conducted. The conjugate $^{19}$F-10 formed immediately, and then slowly isomerized to 1,4-dihydropyrazine $^{19}$F-11 as a mixture of isomers (Scheme 3, showing the corresponding $^{18}$F compounds). These isotopically stable conjugates served as co-injection standards for analysis of reactions with $^{18}$F-9.

Scheme 3 Conjugation between 9 and 1a occurs rapidly to form conjugate 10, which slowly rearranges to 11 as a mixture of regio- and stereoisomers.

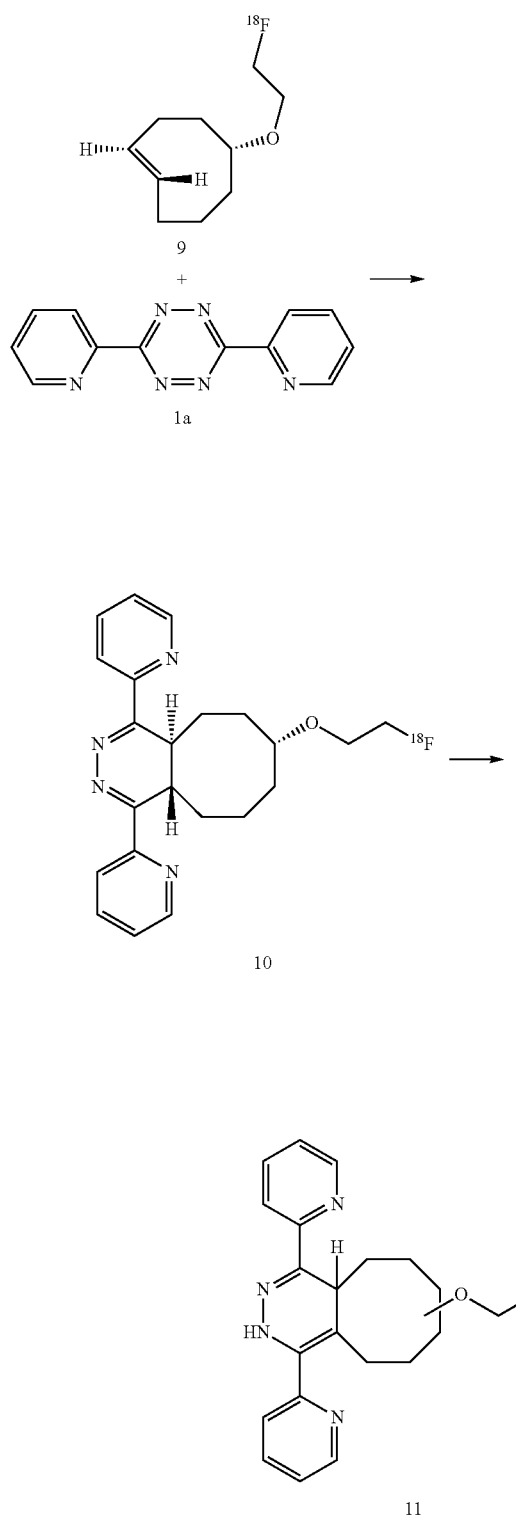

When $^{18}$F-9 (1 mCi, 2 μM) was combined with 1a (concentrations of ≥21 μM), $^{18}$F-9 was completely consumed with 10 s, and $^{18}$F-10 had formed in 98% radiochemical yield, accompanied by $^{18}$F-11 (1%) (Table 2, entries 1-2). When the concentration of $^{18}$F-9 was decreased to 0.1 mCi (0.2 μM), the conjugate $^{18}$F-10/11 was still formed in excellent radiochemical yield (98%, entry 3). Useful radiochemical yields could also be obtained with even lower concentrations of 1a (entries 4-5). The inventors also investigated the efficiency of the conjugation between 1a (21 μM) and $^{18}$F-9 (1 mCi, 2 μM) in PBS buffer and serum media, and found formation of $^{18}$F-10 in quantitative yield within 10 seconds (entries 6-7).

TABLE 2

The effect of concentration on the formation of $^{18}$F-10 through the conjugation between $^{18}$F-9 and 3,6-di(2-pyridyl)-s-tetrazine. All reactions were performed at room temperature.

| Entry | $^{18}$F-9$^a$ | 1a | Solvent | Reaction time | Radiochemical Yield ($^{18}$F-10 + $^{18}$F-11) |
|---|---|---|---|---|---|
| 1 | 1 mCi (2 μM) | 210 μM | MeCN/H$_2$O | <10 s | >98% |
| 2 | 1 mCi (2 μM) | 21 μM | MeCN/H$_2$O | <10 s | >98% |
| 3 | 0.1 mCi (0.2 μM) | 21 μM | MeCN/H$_2$O | <10 s | 98% |
| 4 | 0.1 mCi (0.2 μM) | 2.1 μM | MeCN/H$_2$O | <10 s | 56% |
| 5 | 0.1 mCi (0.2 μM) | 0.21 μM | MeCN/H$_2$O | <10 s | 15% |
| 6 | 1 mCi (2 μM) | 21 μM | PBS buffer | <10 s | >98% |
| 7 | 1 mCi (2 μM) | 21 μM | Serum | <10 s | >98% |

$^a$The concentration of $^{18}$F-9 was estimated based on the specific activity of fluoride after bombardment (~4 Ci/μmol), taking into account a correction for the rate of radioactive decay.

The Diels-Alder conjugate 10 was found to be stable in water, and the benign isomerization to 11 was the only side reaction. Thus, $^{19}$F-10 was the only product detected by $^1$H NMR analysis immediately after the conjugation. In CD$_3$CN/H$_2$O, the rearrangement of $^{19}$F-10 to $^{19}$F-11 proceeded to 11% conversion after 4 hours, and >95% conversion after 48 hours. The stability of the radiolabeled conjugation product was monitored in PBS buffer and serum media for 4 hours, and no degradation products of $^{18}$F-10 were observed.

$^{18}$F-Labeling of Biomolecules

As will now be described, biomolecules may be readily radiolabeled using bioconjugation based on the above-described TTCO-ligation methods and compositions. This makes possible reliable methods for $^{18}$F-labeling of biomolecules in PET and other in vivo applications. In one embodiment, the invention provides a protein or peptide having covalently attached thereto a cyclooctane bearing an $^{18}$F-containing substituent.

Herein, the inventors report the construction of a $^{18}$F labeled PET probe for imaging (such as cancer imaging) based on the tetrazine-trans-cyclooctene ligation.

The conjugations between 1a and $^{18}$F-9 were carried out in 1:1 acetonitrile/water, and were analyzed within 10 seconds of mixing. Prior to the conjugation, $^{18}$F-9 was purified by HPLC and easily separated from unreacted precursor 8.

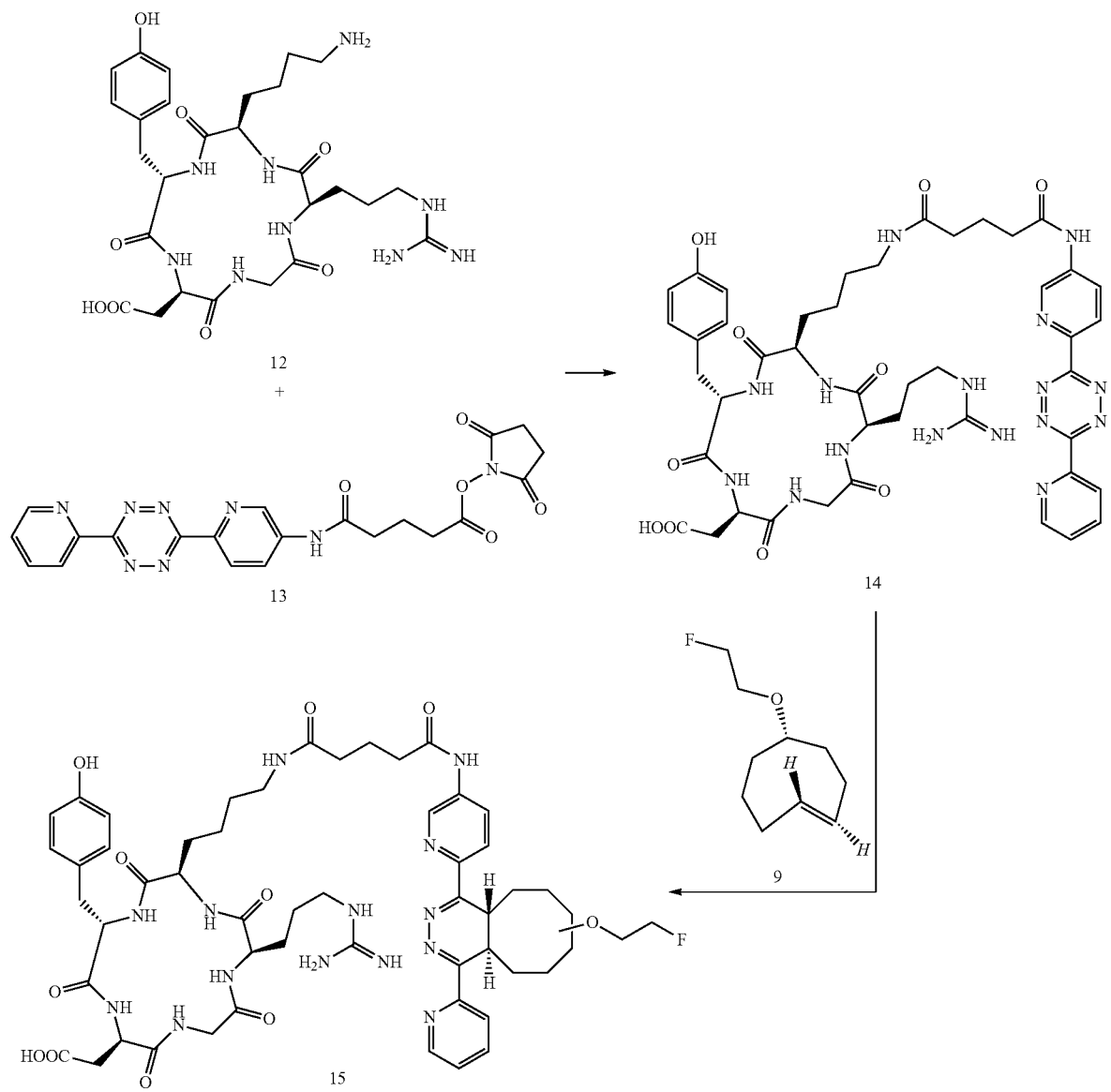

The integrin $\alpha_v\beta_3$ is upregulated on the endothelial surface of tumor blood vessels, and has been linked to tumor progression and metastasis. Radiolabeled synthetic RGD antagonists of the integrin $\alpha_v\beta_3$ have been shown to be effective tools for cancer imaging. Although strategies for F-18 incorporation into RGD mimics are known in the art, they typically involve lengthy synthetic procedures. Consequently, it is challenging to obtain high radiochemical yields and to develop synthetic protocols that can be automated. It has now been found that F-18 labeled RGD peptides can be constructed using tetrazine-trans-cyclooctene ligation, thus allowing cancer detection, patient stratification, and treatment monitoring through PET imaging of integrin $\alpha_v\beta_3$ expression in vivo. One way of doing this involves the use of labeling with $^{18}$F as shown in Scheme 4.

As shown in Scheme 4, tetrazine-RGD conjugate 14 was readily prepared by coupling NHS-ester 13 and the peptide c(RGDyK) (12). To provide an LC-standard, the tetrazine-RGD conjugate 14 was then combined with $^{19}$F-TCO (9) to provide $^{19}$F-15 as a mixture of isomers (due to isomerization of the initially formed 4,5-dihydropyridazine to the corresponding 1,4-dihydropyridazine).

Cell binding affinity studies of c(RGDyK) (12) and $^{19}$F-15 were conducted (FIG. 1). Both peptides inhibited the binding of $^{125}$I-echistatine to U87MG cells (integrin $\alpha_v\beta_3$-positive human glioblastoma) in a dose dependent manner. The IC$_{50}$ values for c(RGDyK) and $^{19}$F-tetrazine-RGD were $(1.16\pm0.35)\times10^{-7}$ and $(1.93\pm0.27)\times10^{-7}$M, respectively, indicating that the fluorinated label had only a minimal effect on the integrin binding affinity of the RGD moiety of 15.

The reaction speed for labeling tetrazine-RGD peptide 14 with $^{18}$F-9 was then investigated. $^{18}$F-9 was synthesized from nosylate 8. The conjugation of $^{18}$F-9 and tetrazine-RGD was performed at room temperature for 5 min. The conjugation was efficient and high yielding: starting with only 30 μg (78 μM) of tetrazine-RGD conjugate 14 and 2 mCi (5 μM) of $^{18}$F-trans-cyclooctene, the labeling yield was 90% after 5 min by HPLC analysis. The stability of $^{18}$F-tetrazine-RGD conjugate 15 was evaluated in PBS in the presence 5% EtOH. The stability was excellent: >95% of the tracer remained after incubation for 6 h as judged by radio-HPLC analysis.

Static microPET scans were performed for $^{18}$F-tetrazine-RGD conjugate 15, via injection into athymic female nude mice bearing an U87MG tumor. High tumor accumulation was observed as early as 30 min time point. The tumor uptake was 4.6±0.2, 4.4±0.6, 4.2±0.6, and 2.7±0.5% ID/g at 0.5, 1, 2, 4 h post injection, respectively. $^{18}$F-15 was cleared through both liver and kidney. Up to 4 h post injection, there was still a fair amount of activity accumulated in the abdomen, which may be a result of the relative hydrophobicity of this system.

Blocking experiments were also performed by co-injecting 10 mg/kg of c(RGDyK) along with $^{18}$F-15. The tracer uptake in U87MG tumor dropped to 1.4±0.2, 1.0±0.3, 0.6±0.2, and 0.4±0.1% ID/g at 0.5, 1, 2, 4 h post injection respectively. The successful blocking confirmed the integrin $\alpha_v\beta_3$ specific binding of the tracer $^{18}$F-15.

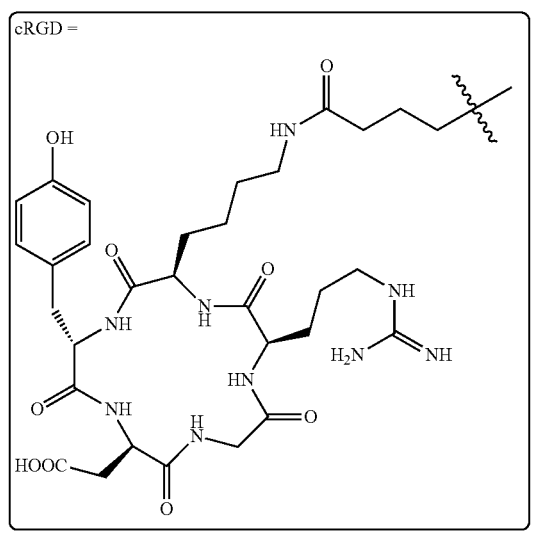 [SMILES: *CCCC(=O)NCCCC[C@H]1NC(=O)[C@@H](CCCNC(=N)N)NC(=O)CNC(=O)[C@@H](CC(=O)O)NC(=O)[C@H](Cc2ccc(O)cc2)NC1=O]

In another example, the conjugation of 18 with 9 to give conjugate 19 is extremely rapid and extremely efficient, and conjugate 19 oxidized spontaneously in solution to form the aromatized compound 20.

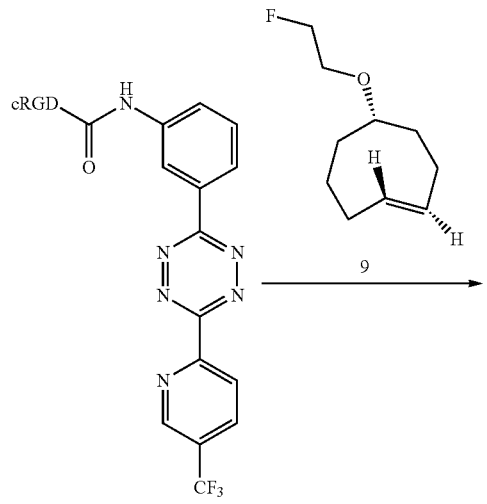

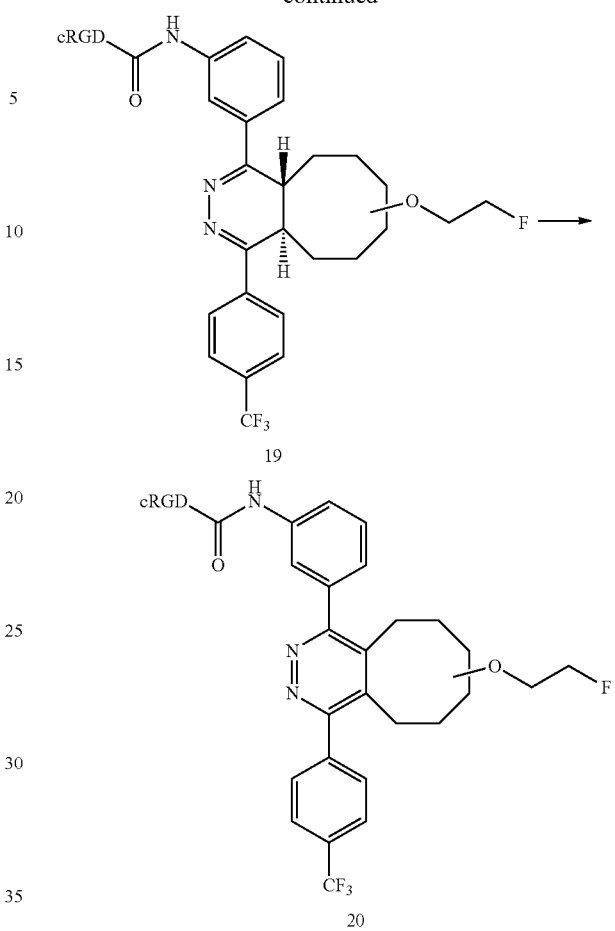

An in vivo metabolic study of 19 was carried out by injecting $^{18}$F-labeled 19 into an athymic nude mouse that was sacrificed 2 h post injection. Major tissues were collected and homogenized. The activity was extracted (CH$_3$CN), filtered (C18 Sep-Pak cartridge), evaporated and analyzed by HPLC. Fractions were collected each minute and radioactivity measured with the γ-counter and analyzed by HPLC. The average fraction of intact tracer was significantly improved compared with compound 15, which showed significant hydrophilic degradation product. For $^{18}$F-19, a hydrophilic byproduct was not observed.

No defluoridation of $^{18}$F-19 was observed as no visible bone uptake was observed in any of the microPET scans. $^{18}$F-19 exhibited good metabolic stability in vivo, and injection of $^{18}$F-19 into a U87MG mouse model resulted in an effective method for $\alpha_v\beta$ imaging. The integrin $\alpha_v\beta_3$ receptor specificity was confirmed by blocking experiments, in which unlabeled cRGD was administered prior to the injection of the $^{18}$F-19.

In a further example, the inventors have synthesized the diaminotetrazine 21 and derivative 22, which can be expected to show rapid conjugation with trans-cyclooctenes such as 9 while affording robust in vivo stability.

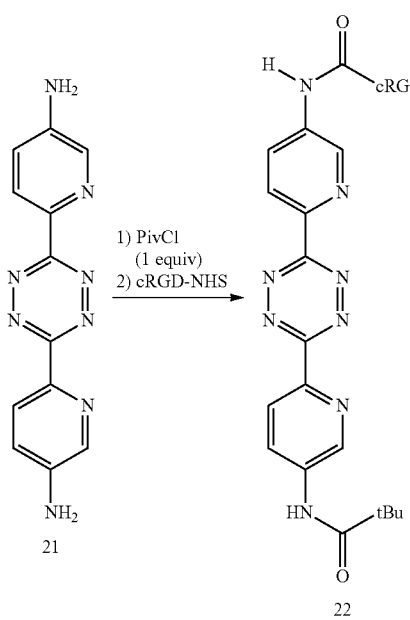

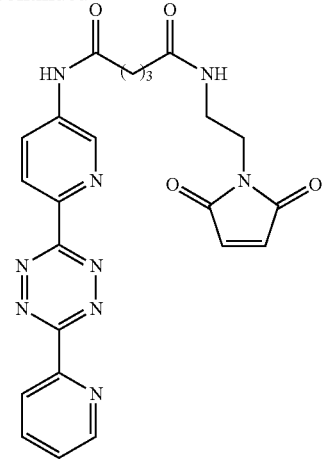

In another aspect, the invention provides efficient methods for conjugating tetrazine and trans-cyclooctenes to proteins. As shown below, the amine-reactive NHS-ester 13 can be readily converted into the thiol-reactive maleimide derivative 24. The reactive functionalities of these molecules may be used to conjugate tetrazines to lysine and cysteine residues of proteins, for example a VEGF protein. NHS-ester 13 can be prepared from 5-oxo-5-(6-(6-(pyridin-2-yl)-1,2,4,5-tetrazin-3-yl)pyridin-3-ylamino)pentanoic acid, in turn prepared by the method of R. Rossin, P. R. Verkerk, S. M. v. d. Bosch, R. C. M. Vulders, I. Verel, J. Lub and M. S. Robillard, *Angew. Chem. Int. Ed.* 2010, 49, 3375-3378.

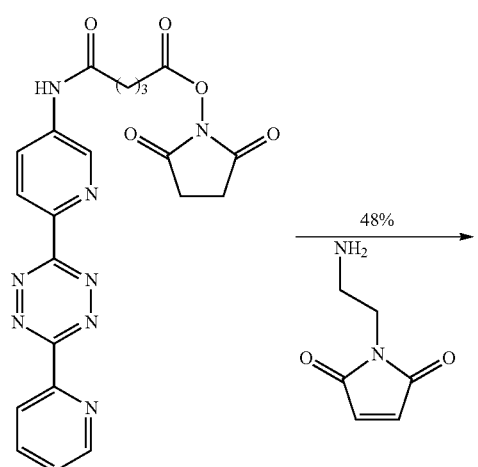

Similarly, the inventors have prepared the amine-reactive (25) and thiol-reactive (26, 27) bifunctional conjugates of trans-cyclooctenes shown below. Compound 25 was readily accessed in 62% yield by the reaction of 16 with 4-nitrophenyl chloroformate. Treatment of 25 with n-(2-aminoethyl)maleimide trifluoroacetate salt yielded 26 in 32% yield. Compound 27 was prepared according to the method of M. L. Blackman, M. Royzen and J. M. Fox, *J. Am. Chem. Soc.* 2008, 130, 13518-13519.

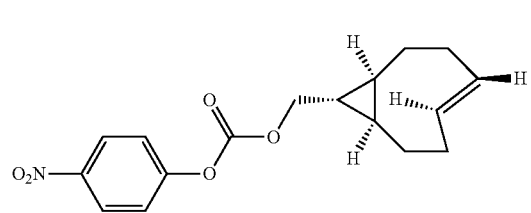

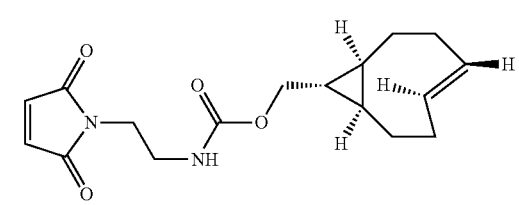

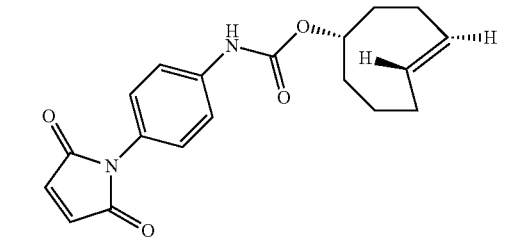

The inventors have conjugated maleimides 26 and 27 to a protein (thioredoxin) using standard methods known in the art, and the conjugates have been shown to undergo rapid tetrazine ligation in high yield. Other proteins may be similarly conjugated according to the invention. Compound 33, the conjugate of 27 with thioredoxin, was rapidly adducted with 3,6-di(2-pyridyl)-s-tetrazine (1a) as shown below, where Trx represents a thioredoxin residue.

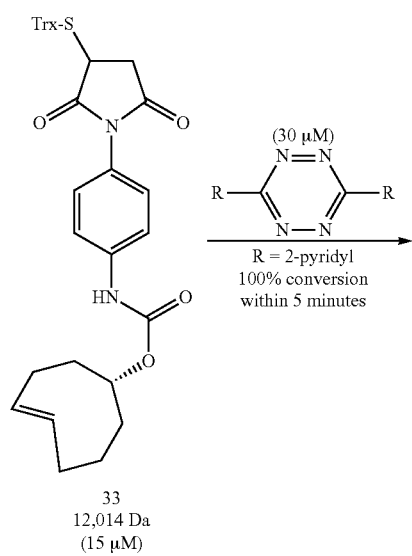
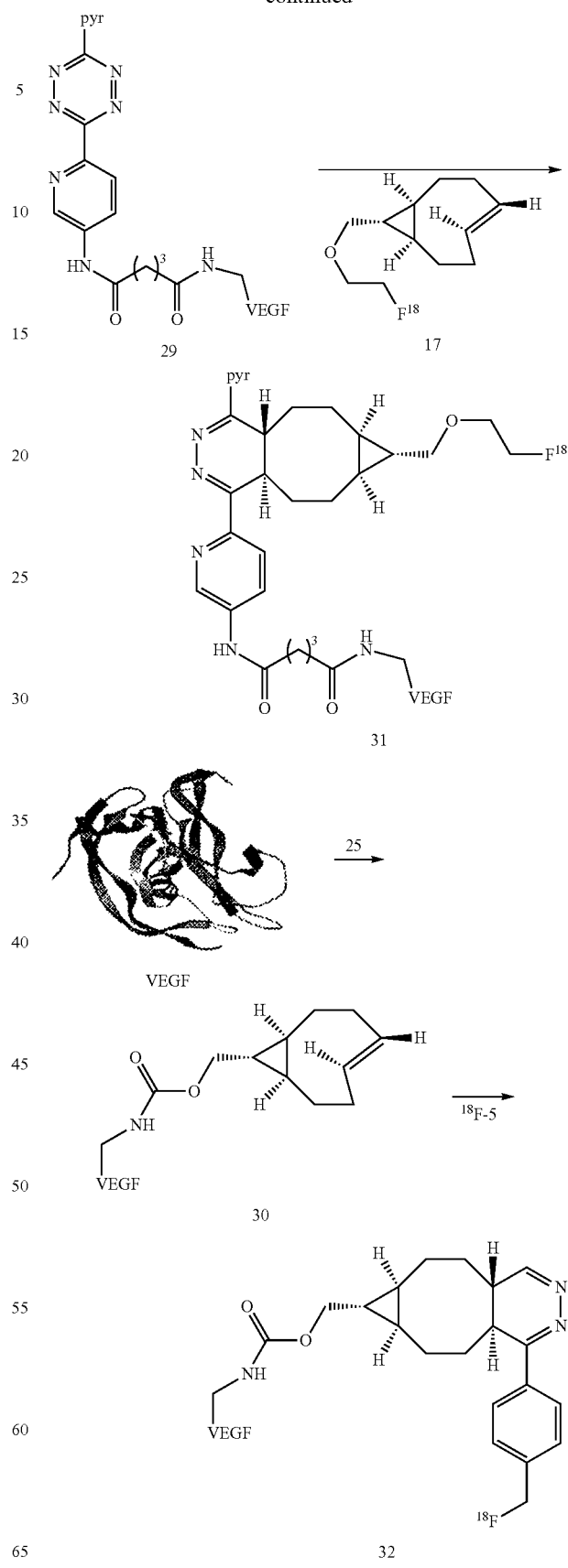
VEGF proteins may be labeled with $^{18}$F via modification of the lysines of wild-type VEGF$_{121}$ protein with amine reactive derivatives (e.g., 24 or 25). The resulting conjugation products (29 and 30, respectively) may be combined with trans-cyclooctene $^{18}$F-17 and tetrazine $^{18}$F-5 to provide radiolabeled conjugates $^{18}$F-31 and $^{18}$F-32, respectively.
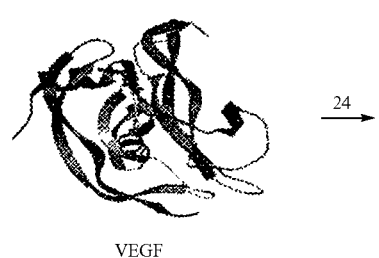

Further exemplary labeled compounds according to the invention include the following.

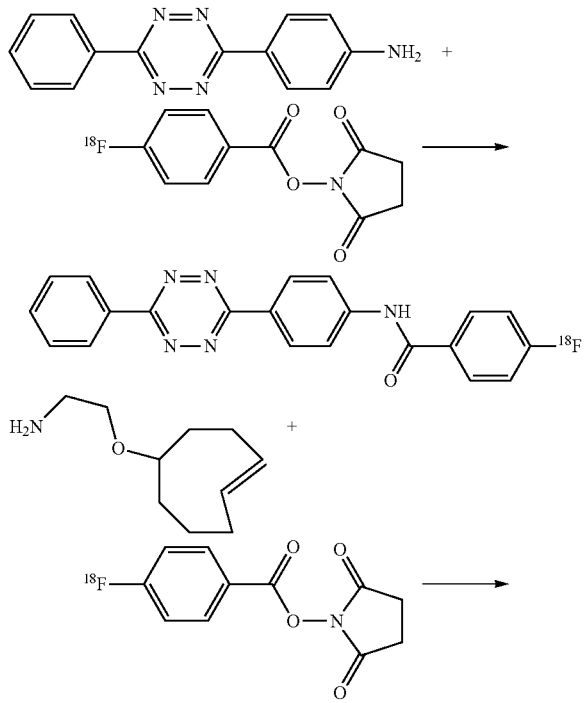

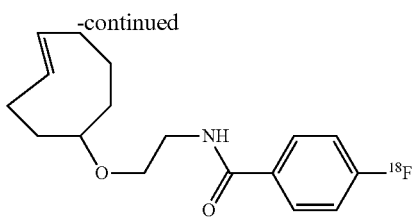

The foregoing results demonstrate an efficient labeling method for PET or other probe construction based on tetrazine-trans-cyclooctene ligation using the methods and compositions of the invention. A major advantage of these techniques lies in the ability to achieve fast and efficient bioconjugation at low concentration. Although the above examples employ specific exemplary biomolecules, the methods and compositions described herein are not limited to those embodiments and labeling of any biomolecule is within the scope of the invention. Other nonlimiting examples of suitable biomolecules that may be labeled include peptides, proteins, antibodies, antibody fragments, and modified oligonucleotides, among others.

Labeling of biomolecules with radionuclides using tetrazine-trans-cyclooctene ligation is not limited to the specific trans-cyclooctenes and tetrazines discussed above; any radiolabeled tetrazine or trans-cyclooctene may be used. The invention encompasses labeling of biomolecules with radionuclides other than $^{18}F$. Suitable further examples of compounds according to the invention, all of which may be used to label biomolecules, include the following.

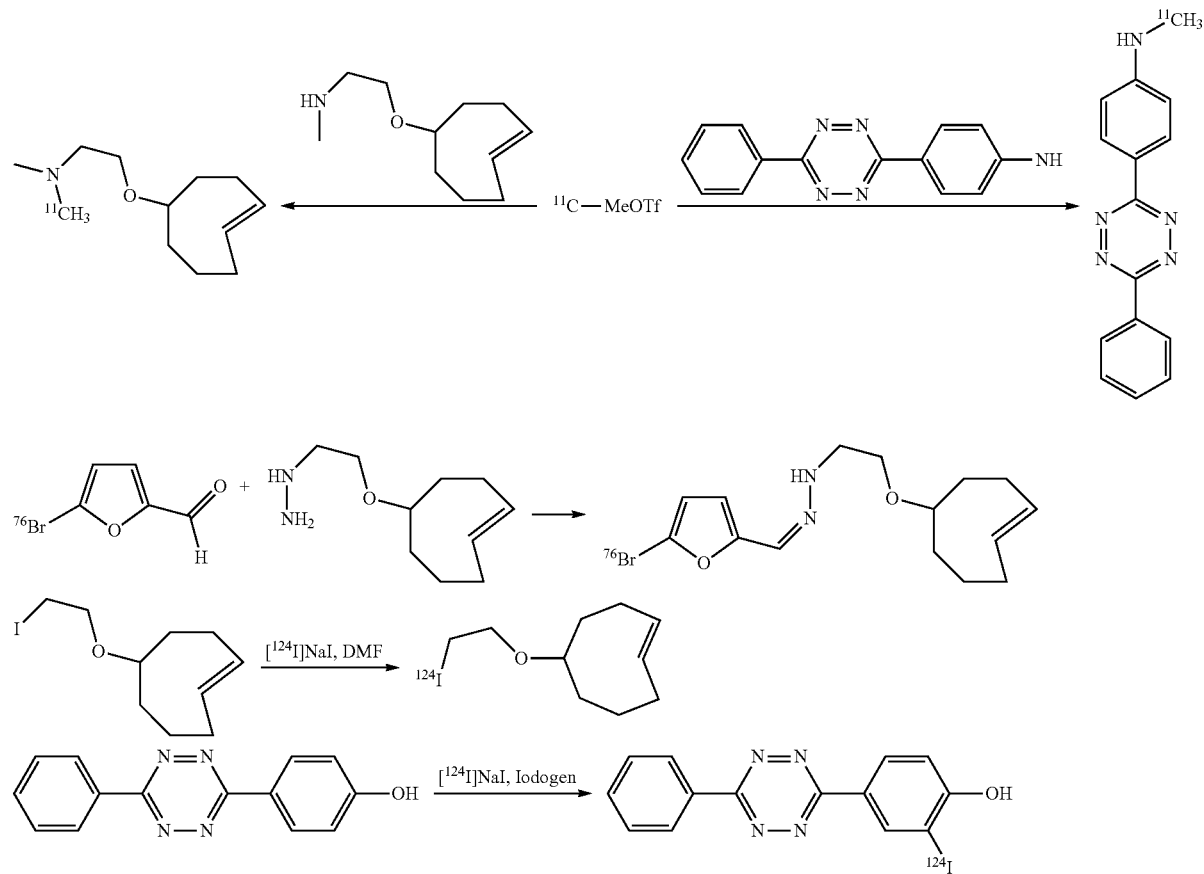

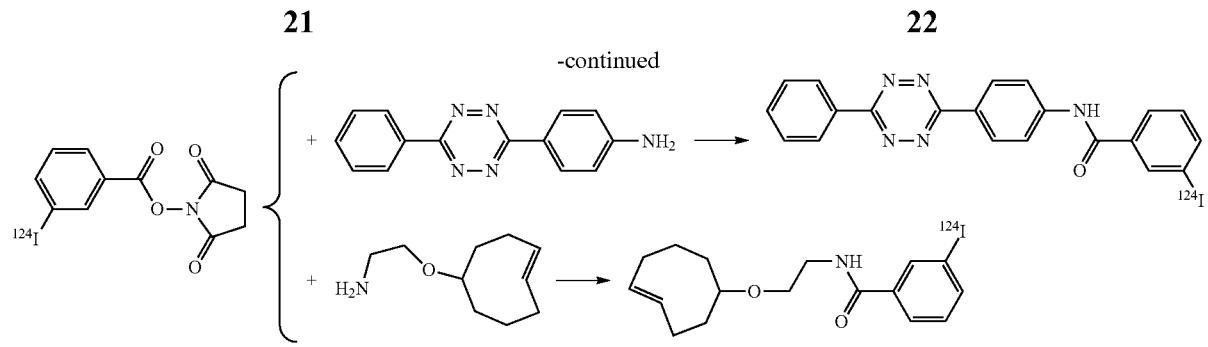

The use of [124]I labeling may for example be suitable for producing PET probes, while $^{125}$I and $^{131}$I may be suitable for preparing SPECT probes.

EXAMPLES

General Considerations

All commercially available chemical reagents were used without further purification. Chromatography was performed using Silacycle P60 silica gel. All moisture sensitive reactions were carried out in glassware that was flame-dried under vacuum and cooled under nitrogen. Solid phase extraction cartridges (silica gel, 900 mg) were purchased from Waters. Ion exchange cartridges were purchased from ABX (Germany).

Z)-2-(cyclooct-4-en-1-yloxy)acetic Acid

Sodium hydride (1.14 g, 26.4 mmol) was added to a flame dried round bottom flask. The NaH was washed with dry hexane (10 mL) and then decanted. Dry tetrahydrofuran (15 mL) was added and the mixture was allowed to stir at room temperature. cis-Cyclooctene-4-ol (P. Lombardi, *Chemistry and Industry* 1990, 21, 708) (0.834 g, 6.61 mmol) in tetrahydrofuran (10 mL) was added to the flask. The mixture was stirred and heated to reflux for 1 hour. α-Bromoacetic acid (0.919 g, 6.61 mmol) in tetrahydrofuran (25 mL) was added and the mixture was allowed to reflux overnight. The mixture was cooled to room temperature, and then concentrated on a rotary evaporator. The residue was cooled in an ice bath and water was added followed by acidification with 3 M HCl. The aqueous layer was extracted with three portions of ether. The extracts were dried with $MgSO_4$ and concentrated in vacuo to provide an oil. The title compound was used directly for the next reaction without further purification.

$^1$H NMR (400 MHz, $C_6D_6$) δ 5.83 (br s, 1H), 5.55-5.43 (m, 2H), 3.70 (d, $J_{AB}$=16.7 Hz 1H), 3.67 (d, $J_{AB}$=16.7 Hz, 1H), 3.19-3.14 (m, 1H), 2.11-2.07 (m, 1H), 1.99-1.84 (m, 2H), 1.80-1.69 (m, 2H), 1.67-1.53 (m, 2H), 1.45-1.34 (m, 2H), 1.19-1.08 (m, 1H).

$^{13}$C NMR (100 MHz, $C_6D_6$) δ 174.7 (C), 130.2 (CH), 129.5 (CH), 81.8 (CH), 65.6 ($CH_2$), 34.0 ($CH_2$), 33.1 ($CH_2$), 25.8 ($CH_2$), 25.5 ($CH_2$), 22.7 ($CH_2$).

IR (liquid, $CHCl_3$, $cm^{-1}$) 3235, 2933, 2859, 1733, 1619, 1453, 1330, 1162, 1133, HRMS-ESI m/z: [M+Na] calcd for $C_{10}H_{16}O_3Na$, 207.0997; found 207.0994.

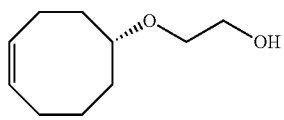 [SMILES: OCCO[C@H]1CC/C=C\CCC1]

(Z)-methyl 2-(cyclooct-4-en-1-yloxy)acetate

An Erlenmeyer flask was sequentially charged with (Z)-2-(cyclooct-4-en-1-yloxy)acetic acid (1.45 g, 7.90 mmol) and diethyl ether (150 mL). Diazomethane was introduced to this flask using the apparatus developed by Lombardi.[1] Thus, Diazald (5.07 g, 23.7 mmol) and ethanol (150 mL) were added to a stoppered flask, equipped to bubble into the aforementioned Erlenmeyer flask. The ethanol mixture was sparged with nitrogen, and a blast shield was placed in front of the two flasks. Sodium hydroxide (7.30 g, 182 mmol) in water (10 mL) was slowly added via syringe to the ethanol-containing flask. Nitrogen was bubbled through this Lombardi flask until no yellow color persisted in either flask. The reaction was purified by column chromatography using 5% ether to 30% ether in hexanes as the eluent to give 1.08 g (69%, 5.47 mmol) of the title compound as a colorless oil.

$^1$H NMR (400 MHz, $C_6D_6$) δ 5.61-5.45 (m, 2H), 3.84 (d, $J_{AB}$=16.6 Hz, 1H), 3.84 (d, $J_{AB}$=16.6 Hz, 1H), 3.37 (app dt, J=4.1, 9.1 Hz, 1H), 3.29 (s, 3H), 2.22-2.13 (m, 1H), 2.05-1.78 (m, 5H), 1.75-1.65 (m, 1H), 1.60-1.46 (m, 2H), 1.30-1.20 (m, 1H).

$^{13}$C NMR (100 MHz, $C_6D_6$) δ 171.0 (C), 130.4 (CH), 129.5 (CH), 81.5 (CH), 66.1 ($CH_2$), 51.0 ($CH_3$), 34.3 ($CH_2$), 33.4 ($CH_2$), 26.0 ($CH_2$), 25.8 ($CH_2$), 22.8 ($CH_2$).

IR (liquid, $CHCl_3$, $cm^{-1}$) 3155, 3019, 2978, 2934, 2860, 1753, 1440, 1383, 1291, 1216, 1129, 900, 722, 650.

HRMS-CI ($NH_3$) m/z: [M+$NH_4$] calcd for $C_{11}H_{22}NO_3$, 216.1599; found 216.1590.

(Z)-2-(cyclooct-4-en-1-yloxy)ethanol (6)

(Z)-methyl 2-(cyclooct-4-en-1-yloxy)acetate (2.34 g, 11.9 mmol) and anhydrous ether (150 mL) were sequentially added to a dry round bottom flask. The flask was cooled to −78° C. DIBAL (9.03 mL, 47.6 mmol) in ether (30 mL) was added slowly via syringe to the flask. The reaction mixture was allowed to stir for another 3 hours at −78° C., then warmed to 0° C. and stirred for a further 3 hours. The reaction was quenched at 0° C. with Na$_2$SO$_4$.10 H$_2$O. The mixture was concentrated in vacuo. The reaction was purified by column chromatography using 5% ether to 30% ether in hexanes as the eluent to give 1.55 g (78%, 9.31 mmol) of the title compound as a colorless oil.

$^1$H NMR (400 MHz, C$_6$D$_6$) δ 5.61-5.48 (m, 2H), 3.54-3.51 (m, 2H), 3.22-3.15 (m, 3H), 2.19-2.13 (m, 1H), 2.03-1.92 (m, 3H), 1.85-1.74 (m, 3H), 1.68-1.62 (m, 1H), 1.51-1.44 (m, 2H), 1.25-1.20 (m, 1H).

$^{13}$C NMR (100 MHz, C$_6$D$_6$) δ 130.4 (CH), 129.5 (CH), 80.9 (CH), 69.8 (CH$_2$), 62.2 (CH$_2$), 34.5 (CH$_2$), 33.4 (CH$_2$), 26.1 (CH$_2$), 25.8 (CH$_2$), 22.9 (CH$_2$).

IR (liquid, CHCl$_3$, cm$^{-1}$) 3456, 3011, 2975, 2936, 2861, 1650, 1447, 1392, 1252, 1100, 1049, 988, 875.

HRMS-ESI m/z: [M+Na] calcd for C$_{10}$H$_{18}$O$_2$Na, 193.1204; found 193.1205.

Major Diastereomer:

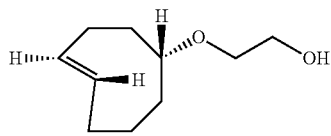

2-[rel-(1R-4E-pR)-cyclooct-4-en-1-yloxy]ethanol (7)

Minor Diastereomer:

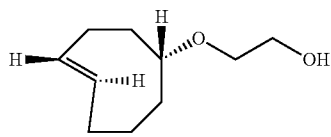

2-[rel-(1R-4E-pS)-cyclooct-4-en-1-yloxy]ethanol (7)

(Z)-2-(cyclooct-4-en-1-yloxy)ethanol (1.54 g, 9.31 mmol) and methyl benzoate (2.49 g, 18.6 mmol) were dissolved in 500 mL of 9:1 ether:hexane in a quartz flask. The photoisomerization was carried out using the flow apparatus described in M. Royzen, G. Yap, and J. Fox, J. Am. Chem. Soc. 2008, 130 (12), 3760.]. The following minor modifications were made: a Biotage "SNAP cartridge" column (50 g, Biotage part no. FSKO-1107-0050) was used, and the FMI pump was a model QG 400. The column was packed with 8.5 cm of silica gel, and then silver impregnated silica gel (16 g) on top. The column was flushed with 9:1 ether:hexane (250 mL). The pump was turned on at a flow rate of 100 mL/min and irradiation begun. Photoisomerization of the mixture was carried out for 6 hours. The column was flushed with 9:1 ether:hexane (250 mL) and then dried with compressed air. The silica was placed into an Erlenmeyer flask and stirred with ammonium hydroxide (200 mL) and methylene chloride (200 mL) for 5 min. The silica gel was filtered and the filtrate was placed into a separatory funnel. The organic layer was separated, and the ammonium hydroxide layer was extracted three times with methylene chloride. The organic layers were combined and twice washed with water. The organic layers were dried with MgSO$_4$, filtered, and purified by column chromatography with 5% ether to 30% ether in hexanes. Two diastereomers were isolated 0.572 g (3.44 mmol, 37%) of 2-[rel-(1R-4E-pR)-cyclooct-4-en-1-yloxy]ethanol and 0.275 g (1.66 mmol, 18%) of 2-[rel-(1R-4E-pS)-cyclooct-4-en-1-yloxy]ethanol as colorless oils. The major diastereomer was contaminated by 7% of the cis-isomer: peaks attributable to cis-isomer 5.61-5.48 (m), 1.51-1.44 (m). The structures were assigned on the basis of the chemical shift for the C-1 methine, as described by M. Royzen, G. Yap, and J. Fox, J. Am. Chem. Soc. 2008, 130 (12), 3760.

Spectroscopic properties of the minor diastereomer:
$^1$H NMR (400 MHz, C$_6$D$_6$) δ 5.75-5.68 (m, 1H), 5.44-5.36 (m, 1H), 3.56 (m, 2H), 3.31-3.29 (m, 1H), 3.28-3.21 (m, 1H), 3.16-3.11 (m, 1H), 2.44 (br s, 1H), 2.41-2.31 (m, 1H), 2.24-2.21 (m, 1H), 2.12-2.08 (m, 1H), 1.99-1.91 (m, 2H), 1.89-1.71 (m, 2H), 1.63-1.57 (m, 1H), 1.25-1.17 (m, 1H), 0.98-0.91 (m, 1H).

$^{13}$C NMR (100 MHz, C$_6$D$_6$) δ 136.0 (CH), 131.5 (CH), 75.2 (CH), 70.4 (CH$_2$), 62.2 (CH$_2$), 40.4 (CH$_2$), 34.9 (CH$_2$), 33.2 (CH$_2$), 30.2 (CH$_2$), 27.9 (CH$_2$).

IR (liquid, CHCl$_3$, cm$^{-1}$) 3428, 3021, 2923, 2859, 1655, 1442, 1352, 1215, 1135, 1099, 1050, 989, 907, 738

Spectroscopic properties of the major diastereomer:
$^1$H NMR (400 MHz, C$_6$D$_6$) δ 5.56-5.34 (m, 1H), 5.22-5.14 (m, 1H), 3.53-3.52 (m, 2H), 3.22-3.17 (m, 1H), 3.12-3.07 (m, 1H), 2.81-2.77 (m, 1H), 2.20-2.16 (m, 2H), 2.05-2.00 (m, 2H), 1.95-1.92 (m, 1H), 1.81-1.68 (m, 4H), 1.35-1.20 (m, 2H).

$^{13}$C NMR (100 MHz, C$_6$D$_6$) δ 135.5 (CH), 132.2 (CH), 86.0 (CH), 69.6 (CH$_2$), 62.2 (CH$_2$), 41.1 (CH$_2$), 38.0 (CH$_2$), 34.8 (CH$_2$), 33.2 (CH$_2$), 31.9 (CH$_2$).

IR (liquid, CHCl$_3$, cm$^{-1}$) 3449, 3012, 2935, 2861, 1647, 1445, 1353, 1198, 1096, 1050, 993, 968, 797.

HRMS-CI (NH$_3$) m/z: [M+H] calcd for C$_{10}$H$_{19}$O$_2$, 171.1385; found 171.1384.

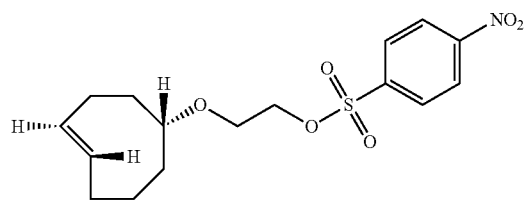

2-[rel-(1R-4E-pR)-cyclooct-4-en-1-yloxy]ethyl 4-nitrobenzenesulfonate (8)

Triethylamine (0.21 mL, 1.5 mmol) was added to a flame dried round bottom flask containing anhydrous ether (5 mL). p-Nitrosulfonyl chloride (0.073 g, 0.33 mmol) from a freshly opened bottle was added to the flask. The mixture was stirred at room temperature for 30 minutes. The mixture was cooled to 0° C. and 2-[rel-(1R-4E-pR)-cyclooct-4-en-1-yloxy]ethanol was added. The mixture was allowed to stir for 5 hours at 0° C. The cold mixture was directly transferred to a column of silica gel. Flash chromatography using a gradient of 5% ether/hexane to 20% ether/hexane as the eluent to afford 0.093 g (87%, 0.26 mmol) of the title compound as a white solid.

In experiments using an aged bottle of p-Nitrosulfonyl chloride, 20% of (R,Z)-2-(cyclooct-4-en-1-yloxy)ethyl 4-nitrobenzenesulfonate was formed. The E-isomer could be separated using preparative, reverse phase HPLC (C-18, 20×250 cm, 65% methanol/H₂O). For ¹⁸F labeling experiments 2-[rel-(1R-4E-pR)-cyclooct-4-en-1-yloxy]ethyl 4-nitrobenzenesulfonate was purified away from the cis isomer.

¹H NMR peaks attributable to the cis isomer: 5.59-5.47 (m)

¹H NMR (400 MHz, C₆D₆) δ 7.50 (m, 4H), 5.34-5.26 (m, 1H), 5.17-5.10 (m, 1H), 3.84-3.82 (m, 2H), 3.05-3.02 (m, 1H), 2.99-2.94 (m, 1H), 2.65-2.61 (m, 1H), 2.17-2.10 (m, 2H), 2.02-1.92 (m, 1H), 1.82-1.77 (m, 1H), 1.74-1.63 (m, 2H), 1.59-1.50 (m, 2H), 1.24-1.12 (m, 2H).

¹³C NMR (100 MHz, C₆D₆) δ 142.0 (C, 2 peaks), 135.8 (CH), 131.2 (CH), 131.2 (CH), 124.1 (CH), 75.3 (CH), 70.4 (CH₂), 65.9 (CH₂), 39.8 (CH₂), 34.7 (CH₂), 33.0 (CH₂), 30.0 (CH₂), 27.6 (CH₂).

IR (liquid, CHCl₃, cm⁻¹) 3105, 3010, 2935, 1609, 1536, 1351, 1187, 1097, 932, 857, 776, 616.

HRMS-LIFDI m/z: [M+] calcd for C₁₆H₂₁NO₆S, 355.1089; found 355.1083.

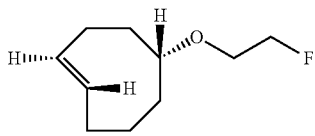

rel-(1R-4E-pR)-5-(2-fluoroethoxy)cyclooct-1-ene
(9)

A dry round bottom flask was sequentially charged with anhydrous acetonitrile (1 mL), 2-[rel-(1R-4E-pR)-cyclooct-4-en-1-yloxy]ethyl 4-nitrobenzenesulfonate (0.0037 g, 0.010 mmol), and TBAF (0.17 mmol, 0.17 mL of a 1M solution in THF). The reaction was heated to 80° C. and allowed to stir for 3 hours. The mixture was cooled and then transferred directly to a column of silica gel. Flash chromatography with a gradient of pentane to 5% ether/pentane as the eluent to afford the title compound. After chromatography, most of the solvents were removed on a rotary evaporator. However, the compound was not dried in vacuo due to volatility. The yield was estimated to be 63% by adding an ¹H NMR standard-mesitylene (0.015 mL, 0.010 mmol). Minor peaks attributable to the cis isomer were detected in the ¹H NMR spectrum at: 5.61-5.47 (m), 1.55-1.47 (m). Minor peaks attributable to the cis isomer were detected by ¹³C NMR at: 130.4, 129.5, 80.9, 34.5, 26.0, 25.8, 22.9, 22.7.

¹H NMR (400 MHz, C₆D₆) δ 5.40-5.33 (m, 1H), 5.22-5.14 (m, 1H), 4.16 (dt, 48 Hz, J$_{HH}$=4.3 Hz, 2H), 3.26-3.21 (m, 2H), 3.19-3.13 (m, 1H), 2.85-2.74 (m, 1H), 2.21-2.14 (m, 2H), 2.09-1.99 (m, 2H), 1.83-1.67 (m, 4H), 1.36-1.21 (m, 2H).

¹³C NMR (100 MHz, C₆D₆) δ 135.6 (CH), 132.2 (CH), 86.2 (CH), 83.2 (d, J$_{C-F}$=169 Hz, CH₂), 67.5 (d, J$_{C-F}$=20 Hz, CH₂), 67.4 (CH₂), 41.1 (CH₂), 38.0 (CH₂), 34.8 (CH₂), 33.2 (CH₂), 31.9 (CH₂).

¹⁹F NMR (376.5 MHz, C₆D₆) δ 222.3

IR (liquid, CHCl₃, cm⁻¹) 3095, 2934, 2860, 1610, 1445, 1191, 1104

HRMS-CI (NH₃) m/z: [M+H] calcd for C₁₀H₁₈OF, 173.1342; found 173.1342.

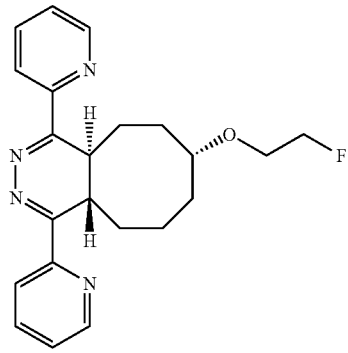 [SMILES: FCCO[C@@H]1CCC[C@@H]2C(c3ccccn3)=NN=C(c3ccccn3)[C@H]2CC1]

7-(2-fluoroethoxy)-1,4-di(pyridin-2-yl)-4a,5,6,7,8,9,10,10a-octahydrocycloocta[d]pyridazine (10)

A dry round bottom flask was charged with 3,6-di(2-pyridyl)-s-tetrazine (0.005 g, 0.02 mmol) and anhydrous acetonitrile (1 mL). The mixture was allowed to stir at room temperature and rel-(1R-4E-pR)-5-(2-fluoroethoxy)cyclooct-1-ene in acetonitrile (0.5 mL) was added dropwise to the flask until yellow color persisted. Flash chromatography using a gradient of 10% acetone/hexane to 60% acetone/hexane as the eluent yielded an 8:2 mixture of 7-(2-fluoroethoxy)-1,4-di(pyridin-2-yl)-4-a,5,6,7,8,9,10,10a-octahydrocycloocta[d]pyridazine and 8-(2-fluoroethoxy)-1,4-di(pyridin-2-yl)-2,4-a,5,6,7,8,9,10-octahydrocycloocta[d]pyridazine in 90% yield, as judged by ¹HNMR. Rearrangement of 10 to 11 occurs at room temperature, so analytical data must be collected within 10 min and without chromatographic purification, to minimize peaks from the rearrangement product.

¹H NMR (400 MHz, CD₃CN) δ 8.73-8.72 (m, 2H), 8.30-8.25 (m, 2H), 7.97-7.86 (m, 2H), 7.48-7.45 (m, 2H), 4.68 (dm, J$_{HF}$=48 Hz, 2H), 4.08-4.03 (m, 1H), 3.98-3.93 (m, 1H), 3.84-3.77 (m, 2H), 3.73-3.70 (m, 1H), 2.18-2.08 (m, 5H), 1.85-1.81 (m, 4H), 1.71-1.62 (m, 1H)

¹⁹F NMR (376.5 MHz, C₆D₆) δ 223.3

HRMS-CI (NH₃) m/z: [M+H] calcd for C₂₂H₂₆N₄OF, 381.2090; found 381.2080.

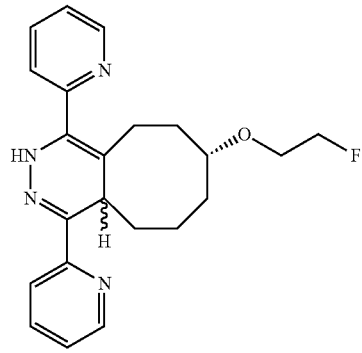 [SMILES: FCCO[C@@H]1CCCC2C(c3ccccn3)=NNC(c3ccccn3)=C2CC1]

8-(2-fluoroethoxy)-1,4-di(pyridin-2-yl)-2,4-a,5,6,7,8,9,10-octahydrocycloocta[d]pyridazine (11)

D₂O (0.1 mL) was added to 7-(2-fluoroethoxy)-1,4-di(pyridin-2-yl)-4-a,5,6,7,8,9,10,10a-octahydrocycloocta[d]

pyridazine in acetonitrile d-3 (1 mL). The mixture was allowed to stand at room temperature for 48 hours. Column chromatography afforded the title compound. $^1$H NMR analysis indicated 97% yield of the title compound.

1H NMR peaks attributable to aliphatic impurity: 1.30, 0.89.

$^1$H NMR (400 MHz, CD$_3$CN) δ 8.99 (br s, 1H), 8.68-8.67 (m, 1H), 8.59-8.57 (m, 1H), 8.09-8.07 (m, 1H), 7.90-7.86 (m, 1H), 7.79-7.74 (m, 1H), 7.65-7.63 (m, 1H), 7.40-7.36 (m, 1H), 7.31-7.28 (m, 1H), 4.51 (dt, J$_{HF}$=48 Hz, J$_{HH}$=4.1 Hz 2H), 4.38-4.34 (m, 1H), 3.75-3.57 (m, 3H), 2.94-2.90 (m, 1H), 2.31-2.27 (m, 1H), 1.91-1.75 (m, 4H), 1.68-1.60 (m, 3H), 1.46-1.37 (m, 2H)

$^{13}$C NMR (100 MHz, CD$_3$CN) δ 155.3 (C), 152.7 (C), 150.3 (CH), 149.6 (CH), 144.1 (C), 137.8 (CH), 137.1 (CH), 135.7 (C), 125.0 (CH), 124.1 (CH), 123.7 (CH), 121.3 (CH), 110.6 (C), 84.5 (d, J$_{C-F}$=165 Hz, CH$_2$), 80.0 (C), 68.1 (d, J$_{C-F}$=19 Hz, CH$_2$), 35.5 (CH), 33.4 (CH$_2$), 31.4 (CH$_2$), 27.0 (CH$_2$), 25.4 (CH$_2$), 22.0 (CH$_2$)

$^{19}$F NMR (376.5 MHz, C$_6$D$_6$) δ 223.3

IR (liquid, CHCl$_3$, cm$^{-1}$) 2934, 2861, 1708, 1599, 1571, 1462, 1361, 1225, 1117, 1047

HRMS-CI (NH$_3$) m/z: [M+H] calcd for C$_{22}$H$_{26}$N$_4$OF, 381.2090; found 381.2085.

HPLC Methods for Analyzing Radiolabeled Materials and Standards

The purification of the crude product was carried out on a analytical reversed-phase high performance liquid chromatography (HPLC) system equipped with a dual UV absorbance detector (Waters 2487) using a Phenomenex C18 RP (150×4.6 mm 5 micron). The flow was 1 mL/min, with the mobile phase starting from 95% solvent A (0.1% TFA in water) and 5% solvent B (0.1% TFA in acetonitrile) (0-2 min), followed by a gradient mobile phase to 5% solvent A and 95% solvent B at 17 min, which was then kept at 95% B until 22 min. The radioactivity was detected by a model of Ludlum 2200 single-channel radiation detector. A semi-preparative C18 reverse phase column (Phenomenex C18) was used in separations with a 4 mL/min flow rate under gradient conditions.

Production of No Carrier Added (NCA) [$^{18}$F]-Fluoride ([$^{18}$F]-F$^-$).

The radioisotope $^{18}$F (t ½=110 m) was prepared by the nuclear reaction $^{18}$O (p, n) to give $^{18}$F in a CTI/Siemens RDS112 11Mev cyclotron. The $^{18}$O is in the form of water with an isotopic purity of greater than 95%. The operation of the cyclotron and target functions was automatically controlled by the cyclotron computer system. The target was loaded with the required amount of [$^{18}$O]-water, and bombarded for the appropriate time with a suitable beam current. The target was then unloaded to a collection vial located in the dose calibrator; where the amount of fluoride was measured. The fluoride solution was then transferred to the chemistry operation.

General Fluorination Method

Figure 2:
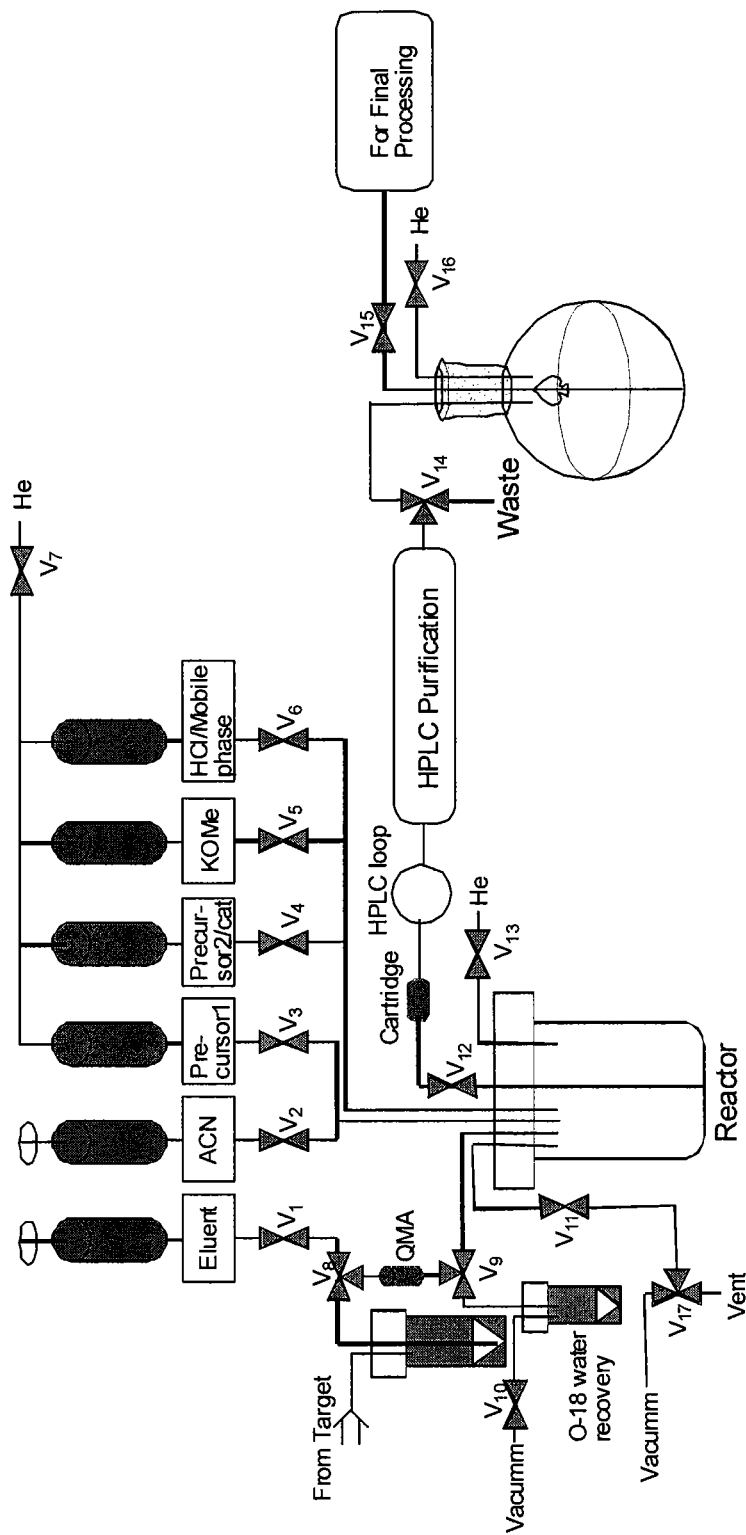
FIG. 2 is a schematic representation of an automated synthesis module for performing fluorination (~200 mCi).

The fluorination (~200 mCi) was performed on an automated synthesis module as shown in FIG. 2. As illustrated in the schematic diagram of the module, two-way valves V1-V6 were used to control the solvent and reagent containing reservoirs 1-6. Reservoirs 3-6 are connected with a nitrogen or argon gas line. Reservoir 1 is connected with reactor through several control valves. The reactor is connected with vacuum pump, gas line, and the injection port of the HPLC system. The solutions of potassium carbonate and Kryptofix K2.2.2 (or TBAB and MeCN) were loaded into Reservoirs 1 and 2, respectively. Reservoirs 3, 4, 5, and 6 were filled with precursor solution and other chemicals/solutions as needed. The target water containing $^{18}$F was passed through a preconditioned QMA cartridge where the $^{18}$F—F$^-$ was trapped. The $^{18}$F was released from the QMA cartridge by passing K$_2$CO$_3$ or TBAB solution from Reservoir 1 through the cartridge and allowed to enter into the reactor. Kyrptofix solution or MeCN from Reservoir 2 was added into the reactor and the whole mixture was dried at 95° C. in combination with nitrogen flow and vacuum. The precursor solution from Reservoir 3 was added to the dried $^{18}$F ion and heated at the desired temperature. The reaction mixture will be sampled out for analysis or loaded on HPLC for purification.

3-(4-(fluoromethyl)phenyl)-s-tetrazine (5)

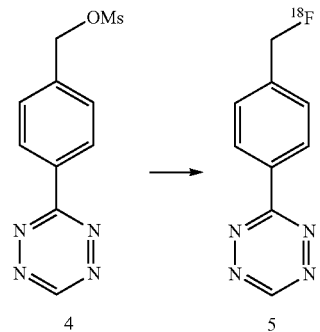 [SMILES: CS(=O)(=O)OCc1ccc(-c2nncnn2)cc1 ; [18F]Cc1ccc(-c2nncnn2)cc1]

F-18 fluoride was dried as described above. Tetrazine 4 was prepared by mesylation of (MsCl, Et$_3$N, CH$_2$Cl$_2$) of 3-(4-hydroxymethyl)-phenyl-s-tetrazine, which had been prepared from 4-hydroxymethylbenzonitrile (formamidine acetate, S$_8$, hydrazine hydrate, then NaNO$_2$/HOAc), according to the method of S. A. Lang Jr., B. D. Johnson, E. J. Cohen, *J. Heterocycl. Chem.* 1975, 12, 1143. Compound 4 was dissolved in MeCN and then allowed to react with $^{18}$F-TBAF at 85° C. for 15 min. The reaction mixture was then analyzed by HPLC. $^{18}$F-5 was eluted off at 15.6 min on HPLC, which correlates with the retention time of the standard compound. The labeling yield was estimated to be 1% (non-decay corrected). Changing the reaction temperature to 110° C. or the solvent to DMSO/DMF did not increase the reaction yield.

General Procedure for Reactions Indicated in Table 1.

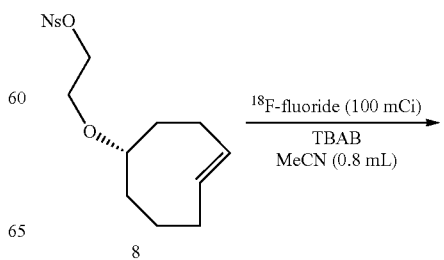

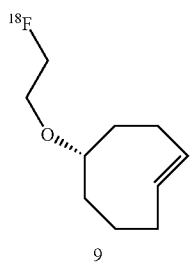

9

Fluoride was dried as described above. Precursor 8 was dissolved in MeCN and added to the azeotropically dried fluoride from Reservoir 3. The crude mixture was heated at desired temperature and then analyzed by HPLC. The optimized labeling conditions are described in entry 3 in table 2. In the automated synthesis, the crude reaction mixture was loaded onto the semi-prep HPLC for separation. The purified sample was injected to the analytical HPLC. [18]F-9 was eluted off at 17.4 min on HPLC, which correlates with the retention time of the standard compound. Under the optimized conditions, the radiochemical purity of [18]F-9 was more than 98%.

General Procedure for Reactions Described in Table 2

HPLC-purified [18]F-9 was mixed with 3,6-Di(2-pyridyl)-s-tetrazine (1a) under the conditions described in Table 2. Immediately after mixing, the crude reaction mixture was analyzed by HPLC. The HPLC injection was made within 10 seconds of mixing. [18]F-10 was eluted off at 11.8 min on HPLC, which correlates with the retention time of the standard compound. Small amounts of isomers [18]F-11 were also observed on the HPLC radio trace. The retention time of peaks attributable to the isomers of [18]F-11 were 12.7 and 13.3 min, which correlates with the retention times for the $^{19}$F standards.

Radiochemistry

[$^{18}$F] Fluoride was prepared by the [18]O(p,n)[18]F nuclear reaction, and it was then adsorbed onto an anion exchange resin cartridge. Kryptofix 222/$K_2CO_3$ solution (1 mL 9:1 acetonitrile/water, 15 mg Kryptofix 222, 3 mg $K_2CO_3$) was used to elute the cartridge, and the resulting mixture was dried in a glass reactor. [18]F-9 was prepared according to reported procedures and purified via semipreparative HPLC. Labeling of tetrazine-RGD conjugate 14 with [18]F-9 was performed in DMSO/EtOH (1:3). The resulting mixture was diluted with water and purified by semi-preparative HPLC. The final product [18]F-15 was concentrated and formulated in saline (0.9%, 500 μL) for in vivo studies.

Cell Line and Animal Models

U87MG human glioblastoma cells were grown in Dulbecco's medium (Gibco) supplemented with 10% fetal bovine serum (FBS), 100 IU/mL penicillin, and 100 μg/mL streptomycin (Invitrogen Co.). Animal procedures were performed according to a protocol approved by the Stanford University Institutional Animal Care and Use Committee. A U87MG xenograft model was generated by subcutaneous (s.c.) injection of $1\times10^7$ U87MG cells (integrin $\alpha_v\beta_3$-positive) into the front flank of female athymic nude mice. Three to four weeks after inoculation (tumor volume: 100-400 $mm^3$), the mice (about 9-10 weeks old with 20-25 g body weight) were used for microPET studies.

Cell Integrin Receptor-Binding Assay

In vitro integrin-binding affinity and specificity of c(RGDyK) and [19]F-15 were assessed via competitive cell binding assays using $^{125}$I-echistatin as the integrin $\alpha_v\beta_3$-specific radioligand. The best-fit 50% inhibitory concentration ($IC_{50}$) values for U87MG cells were calculated by fitting the data with nonlinear regression using *GraphPad Prism* (GraphPad Software, Inc.). Experiments were performed with triplicate samples.

microPET Studies

PET scans and image analysis were performed using a microPET R4 rodent model scanner (Siemens Medical Solutions). About 2 MBq of [18]F-15 was intravenously injected into each mouse (n=3) under isoflurane anesthesia (1-3%) and then subjected to static scans at 0.5, 1, 2, and 4 h p.i. For each microPET scan, regions of interest (ROIs) were drawn over the tumor, normal tissue, and major organs on decay-corrected whole-body coronal images. The radioactivity concentration (accumulation) within a tumor was obtained from the mean value within the multiple ROIs and then converted to % ID/g. For a receptor-blocking experiment, mice bearing U87MG tumors on the front left flank were scanned after co-injection with [18]F-15 and c(RGDyK) (10 mg/kg).

2,5-dioxopyrrolidin-1-yl 5-oxo-5-((6-(6-(pyridin-2-yl)-1,2,4,5-tetrazin-3-yl)pyridin-3-yl)amino)pentanoate (13)

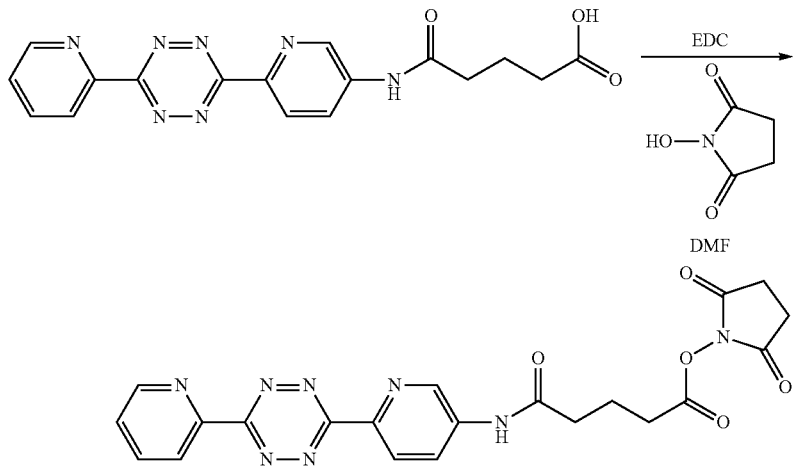

13

A dry 3 mL vial was sequentially charged with 5-oxo-5-((6-(6-(pyridin-2-yl)-1,2,4,5-tetrazin-3-yl)pyridin-3-yl)amino)pentanoic acid (170 mg, 0.46 mmol), 1,2N-hydroxysuccinimide (75 mg, 0.65 mmol) and 1-ethyl-3-(3-dimethylaminopropyl)carbodiimide hydrochloride (115 mg, 0.60 mmol). The vial was capped by a screw cap with a Teflon septum. The vial was swept with nitrogen, and anhydrous DMF (1.5 mL) was added via syringe. The reaction mixture was allowed to stir for 20 h at room temperature. The mixture was then diluted by $CH_2Cl_2$ (5 centrifuged, and the supernatant was decanted. The purple solid was subjected to three further cycles of suspension in $CH_2Cl_2$ (5 mL), centrifugation, and decantation to provide the 130 mg (59%) of the title compound as a purple solid (130 mg, 59%).

$^1$H NMR (400 MHz, DMSO-$d_6$, δ): 10.66 (s, 1H), 9.06 (d, 2.4 Hz, 1H), 8.94 (m, 1H), 8.64 (d, J=8.8 Hz, 1H), 8.60 (dt, J=7.9, 1.0 Hz, 1H), 8.44 (dd, J=8.8, 2.4 Hz, 1H), 8.17 (dt, J=7.9, 1.7 Hz, 1H), 7.74 (ddd, J=7.5, 4.6, 1.0 Hz, 1H), 2.87-2.80 (m, 6H), 2.59 (t, J=7.6 Hz, 2H), 1.99 (q, J=7.6 Hz, 2H);

$^{13}$C NMR (100 MHz, DMSO-$d_6$, δ): 172.0 (C), 170.8 (C), 169.3 (C), 163.5 (C), 163.2 (C), 151.1 (CH), 150.7 (C), 144.4 (C), 141.7 (CH), 138.9 (C), 138.3 (CH), 127.1 (CH), 126.7 (CH), 125.4 (CH), 124.7 (CH), 35.0 ($CH_2$), 30.0 ($CH_2$), 25.9 ($CH_2$), 20.2 ($CH_2$);

HRMS-ESI (m/z): $[M-C_4H_4NO_3]^+$ (acylium ion): calcd for $C_{17}H_{14}N_7O_2$, 348.1209; found: 348.1202.

Tetrazine-RGD Conjugate (14)

A dry 3 mL vial was charged with 13 (5.2 mg, 0.011 mmol) and 12 (3.4 mg, 0.0055 mmol). The vial was capped by a screw cap with a Teflon septum, and the vial was swept with nitrogen. A solution of diisopropylethylamine (1.4 mg, 0.011 mmol) in DMF (30 μL) was added via syringe, followed by the addition of DMF (0.57 mL). The reaction mixture was allowed to stir for 18 h at room temperature. The mixture was then diluted by methanol (1 mL), centrifuged, and the supernatant was decanted. The purple solid was subjected to two further cycles of suspension in methanol (1 mL), centrifugation, and decantation to provide 14 as a purple solid (5.1 mg, 96%). The purity was judged to be 95% by HPLC analysis (Shimadzu C18 column, 4.6 mm×50 mm, 5 micron). HPLC analysis was performed with eluents that contained 0.1% trifluoroacetic acid, eluting at 1 mL/min, initially with 10% acetonitrile/water for 5 min, followed by a gradient of 10%-20% acetonitrile/water for 5 min, and final elution with 20% acetonitrile/water.

HRMS-ESI (m/z): $[M-H]^+$: calcd for $C_{44}H_{64}N_{16}O_{10}^+$, 967.4282; found: 967.4305.

Diels-Alder Adduct ($^{18}$F-15)

A 1.5 mL Eppendorf tube was sequentially charged with tetrazine-RGD conjugate 14 (0.25 mg) in DMSO (0.2 mL) and trans-Cyclooctene $^{18}$F-9 (0.1 mg) in acetonitrile (0.1 mL). The mixture was allowed to stir at room-temperature for 1 min to provide $^{18}$F-15. Purification of the crude product was carried out on an analytical reverse-phase high performance liquid chromatography (HPLC) system equipped with a dual UV absorbance detector (Waters 2487) using a Phenomenex C18 reverse phase column (150×4.6 mm, micron).

HPLC analysis was performed with eluents that contained 0.1% trifluoroacetic acid, eluting at 1 mL/min, initially with 5% acetonitrile/water for 2 min, followed by a gradient of 5%-95% acetonitrile/water for 22 min, and final elution with 95% acetonitrile/water.

The same conditions were used for radio-HPLC analysis of $^{18}$F-15. The radioactivity was detected by a model of Ludlum 2200 single-channel radiation detector. Thus, 2 mCi of $^{18}$F-9 (Li, Z.; Cai, H.; Hassink, M.; Blackman, M. L.; Brown, R. C.; Conti, P. S.; Fox, J. M. *Chem. Commun.* 2010, 46, 8043) in 300 μL EtOH was added to the tetrazine-RGD conjugate 14 (25+/-5 μg, 100 μL DMSO) and the mixture was allowed to sit at room temperature for 1 min. The purification of $^{18}$F-15 was carried out on an analytical reversed-phase HPLC system using the conditions mentioned above.

HRMS-ESI (m/z): $[M-H]^+$: calcd for $C_{54}H_{71}FN_{14}O_{11}$: 1111.5484; found: 1111.5510.

Tetrazine-RGD Conjugate (18)

Tetrazine-RGD conjugate 18 was prepared according to the following sequence.

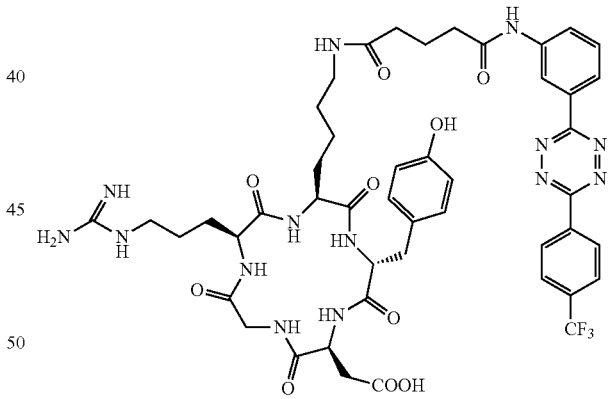

3-nitro-2-[4-(trifluoromethyl)benzoyl]hydrazide (38)

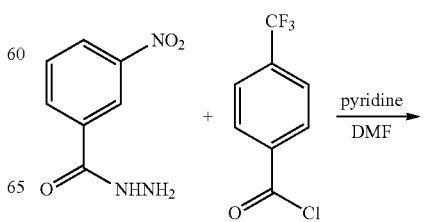

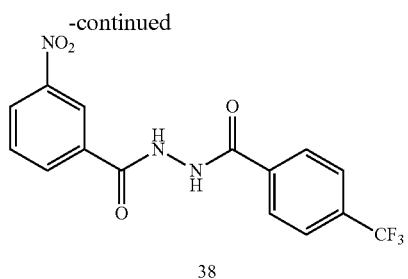

38

To a stirring solution of 3-nitrobenzhydrazide (1.0 g, 5.52 mmol) and pyridine (0.9 mL) in DMF (1.5 mL) in a round-bottom flask under $N_2$ was added 4-(trifluoromethyl) benzoyl chloride (1.3 g, 6.07 mmol) dropwise at 0° C. The reaction mixture was stirred at room temperature for 12 h and then transferred into a beaker containing ice water. The white solid that precipitated out of the solution was isolated by filtration and washed several times with cold $H_2O$. The crude solid was purified by recrystallization with acetone to give 1.6 g (4.4 mmol, 80%) of 38 as a white solid, mp 223-225° C. $^1$HNMR (DMSO-$d_6$, 400 MHz, 5): 11.0 (s, 1H), 10.9 (s, 1H), 8.76 (t, J=2.2 Hz, 1H), 8.47 (dd, J=8.3 Hz, 2.4 Hz, 1H), 8.37 (dd, J=7.9 Hz, 2.4 Hz, 1H), 8.13 (d, J=8.3 Hz, 2H), 7.94 (d, J=8.3 Hz, 2H), 7.87 (t, J=7.6 Hz, 1H). $^{13}$C NMR (DMSO-$d_6$, 100 MHz, 6): 164.7 (u), 163.8 (u), 147.9 (u), 136.1 (u), 133.8 (dn), 133.7 (u), 131.7 (u) [q, $^2$J(CF)= 35.2 Hz], 130.5 (dn), 128.4 (dn), 126.6 (dn), 125.7 (dn) [q, $^3$J(CF)=4.0 Hz], 123.9 (u) [q, $^1$J(CF)=272.6 Hz] 122.2 (dn). IR (neat, KBr, cm$^{-1}$) 3191, 3022, 2847, 1575.1, 1328. HRMS (ESI−) [M−H] calcd. for $C_{15}H_9F_3N_3O_4$ 352.0545; found 352.0536.

N'-(chloro(4-(trifluoromethyl)phenyl)methylene)-3-nitrobenzohydrazonoyl chloride (37)

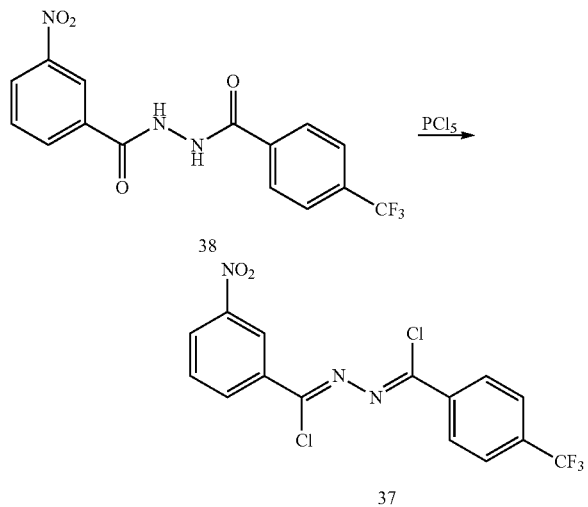

A dry round-bottomed flask was charged with 38 (1.0 g, 2.72 mmol) and the flask was evacuated and filled with nitrogen. Anhydrous dichloroethane (27 mL) and PCl$_5$ (1.7 g, 8.17 mmol) were added to the reaction mixture. The reaction mixture was allowed to reflux and stir for 16 h. The reaction mixture was cooled to room temperature and slowly poured into ice water. The organic and aqueous layers were separated, and the organic layer was washed with saturated NaHCO$_3$, dried over MgSO$_4$, filtered and concentrated in vacuo. The crude residue was chromatographed using a gradient (2-8%, then 20%, 40%) of CH$_2$Cl$_2$ in hexanes to give 0.804 g (2.00 mmol, 73%) of 37 as a yellow solid, mp 78-80° C. $^1$H NMR (CDCl$_3$, 400 MHz, 6): 8.93 (t, J=2.0 Hz, 1H), 8.44 (dd, J=8.0, 1.9 Hz, 1H), 8.38 (dd, J=8.3 Hz, 2.3 Hz, 1H), 8.23 (d, J=8.3 Hz, 2H), 7.71 (d, J=8.4 Hz, 2H), 7.66 (t, J=8.1 Hz, 1H). $^{13}$C NMR (CDCl$_3$, 100 MHz, δ): 148.4 (u), 143.6 (u), 142.2 (u), 136.4 (u), 135.1 (u), 133.9 (dn), 133.6 (u) [q, $^2$J(C—F)=33.4 Hz], 129.8 (dn), 128.9 (dn), 126.4 (dn) [q, $^3$J(CF)=4.0 Hz], 125.6 (dn), 123.6 (u) [q, $^1$J(CF)=274.0 Hz] 123.5 (dn). IR (CHCl$_3$, cm$^{-1}$) 3088, 3059, 1602, 1537, 1326. $C_{15}H_5Cl_2F_3N_3O_2$ 391.1441; found 391.1445.

3-(3-Nitrophenyl)-6-[4-(trifluoromethyl)phenyl]-s-tetrazine (2b)

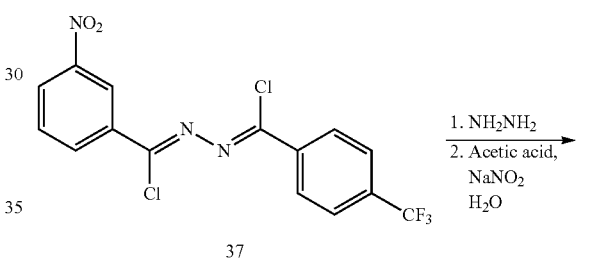

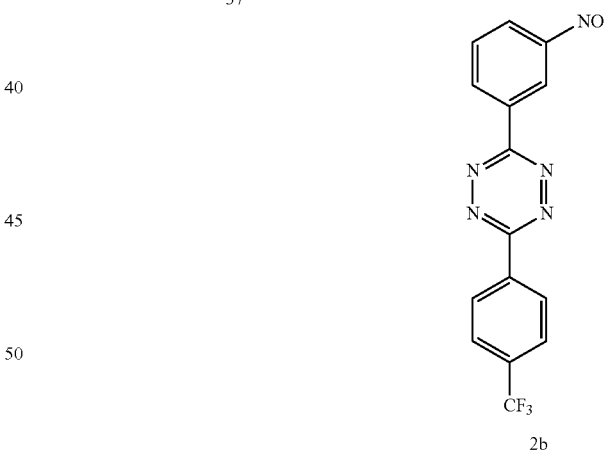

2b

A dry round-bottom flask was charged with 37 (0.804 g, 2.00 mmol), CH$_3$CN (15 mL) and 64% hydrazine hydrate (0.097 mL, 2.00 mmol). The flask was fitted with a reflux condenser, and the mixture was heated to 50° C. for 1 h behind a blast shield. K$_2$CO$_3$ (0.553 g, 4.00 mmol) was added, and the reaction mixture was allowed to reflux and stir for 24 h. 64% hydrazine hydrate (0.291 mL, 6.00 mmol) was added to the mixture, which was allowed to reflux for an additional hour. The reaction mixture was cooled to room temperature. The resulting orange precipitate was isolated by filtration, washed with cold H$_2$O, and dried under vacuum. The crude residue was diluted with glacial acetic acid (4.0 mL) at 0° C., and a solution of NaNO$_2$ (0.690 g, 10.0 mmol) in H$_2$O (1.1 mL) was added dropwise to the solution. The reaction mixture was diluted with CH$_2$Cl$_2$ (100 mL) and washed repeatedly with saturated NaHCO$_3$. The organic solution was dried over MgSO$_4$, filtered, and concentrated in vacuo. The crude residue was concentrated onto silica gel and chromatographed using a gradient (0-30%) of CH$_2$Cl$_2$ in hexanes to give 0.583 g (1.68 mmol, 84%) of 2b as a pink solid, mp 217-219° C. $^1$H NMR (CDCl$_3$, 400 MHz, δ): 9.54 (t, J=2.0 Hz, 1H), 9.01 (dd, J=7.8 Hz, 1.6 Hz, 1H), 8.81 (d, J=8.3 Hz, 2H), 8.51 (dd, J=8.3 Hz, 2.3 Hz, 1H), 7.89 (d, J=8.3 Hz, 2H), 7.84 (t, J=8.1 Hz, 1H). $^{13}$C NMR (CDCl$_3$, 100 MHz, δ): 164.7 (u), 163.4 (u), 147.9 (u), 136.1 (u), 133.8 (dn), 133.7 (u), 131.5 [u (q, $^2$J(C—F)=34.5 Hz)], 130.5 (dn), 126.6 (dn) [q, $^3$J(CF)=4.0 Hz], 125.6 (dn), 123.6 (u) [q, $^1$J(CF)=271.5 Hz], 122.2 (dn). IR (CHCl$_3$, cm$^{-1}$) 2932, 2856, 1531, 1324. HRMS (ESI) [M−H] calcd. for C$_{15}$H$_8$F$_3$N$_5$O$_2$ 347.0630; found 347.0622.

3-(3-Aminophenyl)-6-[4-(trifluoromethyl)phenyl]-s-tetrazine (36)

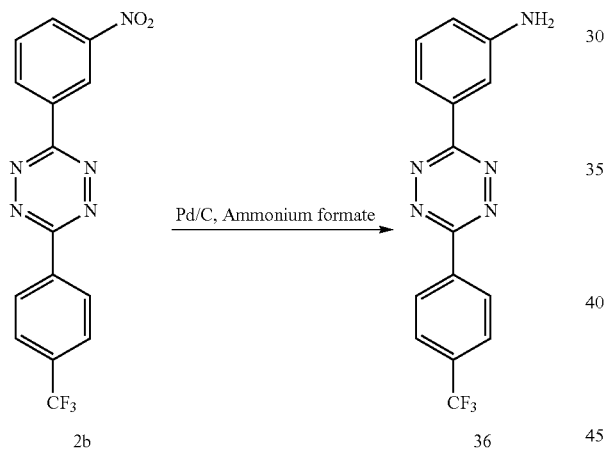

To a stirring solution of 2b (0.010 g, 0.029 mmol) in CH$_3$CH$_2$OH (0.3 mL) under N$_2$ was added ammonium formate (0.006 g, 0.093 mmol) and 5% Pd/C (0.004 g, 0.002 mmol). The reaction mixture was allowed to reflux for 20 h then cooled to room temperature and filtered through celite. The filtrate was concentrated in vacuo, and the crude residue was concentrated onto silica gel and chromatographed using a gradient (0-6%) of acetone in CH$_2$Cl$_2$ to give 0.004 g (0.013 mmol, 44%) of 36 as a red solid, mp 214-216° C. $^1$HNMR (DMSO-d$_6$, 400 MHz, δ): 8.71 (d, J=8.3 Hz, 2H), 8.06 (d, J=8.8 Hz, 2H), 7.81 (t, J=2.0 Hz, 1H), 7.71 (m, J=8.3 Hz, 2.2 Hz, 1H), 7.32 (t, J=7.4 Hz, 1H), 6.89 (dd, J=8.5 Hz, 1.9 Hz, 1H), 5.5 (m, 2H). $^{13}$C NMR (DMSO-d$_6$, 100 MHz, δ): 163.7 (u), 162.4 (u), 149.6 (u), 135.9 (u), 132.0 (u), 131.9 [u (q, $^2$J(C—F)=34.5 Hz)], 128.2 (dn), 130.0 (dn), 126.3 (dn) [q, $^3$J(CF)=4.0 Hz], 121.0 (u) [q, $^1$J(CF)=273.2 Hz], 118.2 (dn), 115.2 (dn), 112.4 (dn). IR (CHCl$_3$, cm$^{-1}$) 3443, 3156. HRMS (ESI) [M+H] calcd. for C$_{15}$H$_{11}$F$_3$N$_5$ 318.0967; found 318.0976.

5-oxo-5-(3-(6-(4-(trifluoromethyl)phenyl)-1,2,4,5-tetrazin-3-yl)phenylamino)pentanoic acid (35)

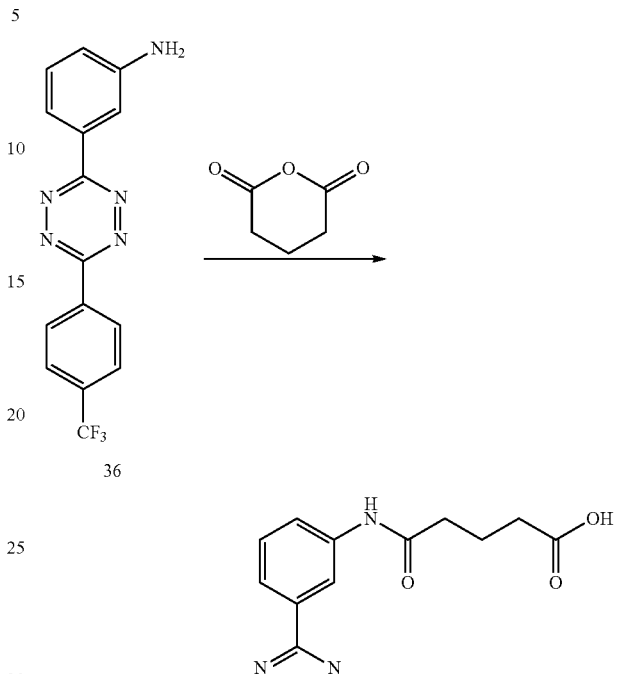

A resealable glass vial was flushed with N$_2$ and charged with 36 (0.010 g, 0.032 mmol), glutaric anhydride (0.018 g, 0.158 mmol) and anhydrous THF (0.3 mL). The vial was capped, and the mixture was stirred at 80° C. for 1 h. The reaction mixture was cooled to room temperature, triturated with CH$_2$Cl$_2$ and hexanes and dried under vacuum to give 0.010 g (0.023 mmol, 72%) of 35 as a pink solid, mp 246-248° C. $^1$H NMR (DMSO-d$_6$, 400 MHz, δ): 10.3 (s, 1H), 8.92 (t, J=1.8 Hz, 1H), 8.74 (d, J=8.2 Hz, 2H), 8.23 (dd, J=7.8 Hz, 1.8 Hz, 1H), 8.09 (d, J=8.2 Hz, 2H), 7.92 (dd, J=8.2 Hz, 2.3 Hz, 1H), 7.63 (t, 1H), 2.43 (t, J=7.1 Hz, 2H), 2.31 (t, J=7.4 Hz, 2H), 1.85 (quin., J=7.0 Hz, 2H). $^{13}$C NMR (DMSO-d$_6$, 100 MHz, δ): 174.3 (u), 171.3 (u), 163.5 (u), 162.6 (u), 140.4 (u), 135.9 (u), 132.0 (u) [q, $^2$J(C—F)=32.5 Hz], 132.0 (u), 130.1 (dn), 128.4 (dn), 126.4 (dn) [q, $^3$J(CF)=4.0 Hz], 124.2 (u) [q, $^1$J(CF)=275.1 Hz], 123.1 (dn), 122.6 (dn), 118.0 (dn), 35.5 (u), 33.1 (u), 20.4 (u). IR (neat, KBr, cm$^{-1}$) 3307, 2952, 1663, 1392. HRMS (ESI) [M+H] calcd. for C$_{20}$H$_{17}$F$_3$N$_5$O$_3$ 431.3679; found 431.3677.

2,5-dioxopyrrolidin-1-yl 5-oxo-5-((6-(6-(pyridin-2-yl)-1,2,4,5-tetrazin-3-yl)pyridin-3-yl)amino)pentanoate (34)

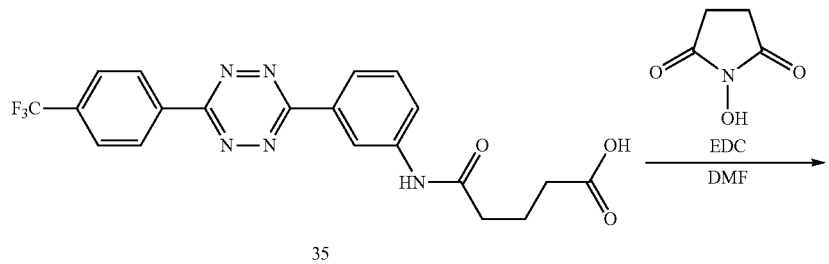

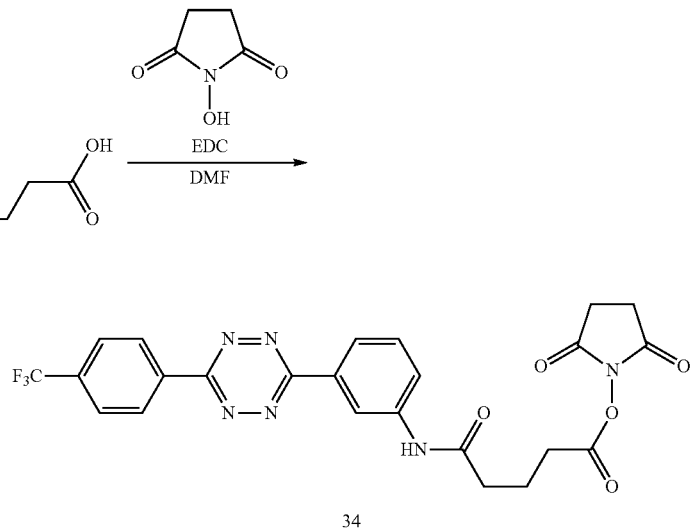

A dry 3 mL vial was sequentially charged with 5-oxo-5-((3-(6-(4-(trifluoromethyl)phenyl)-1,2,4,5-tetrazin-3-yl)phenyl)amino)pentanoic acid (170 mg, 0.46 mmol), N-hydroxysuccinimide (86 mg, 0.20 mmol) and 1-ethyl-3-(3-dimethylaminopropyl)carbodiimide hydrochloride (77 mg, 0.40 mmol). The vial was capped by a screw cap with a Teflon septum. The vial was swept with nitrogen, and anhydrous DMF (1.5 mL) was added via syringe. The reaction mixture was allowed to stir for 34 h at room temperature. The mixture was then diluted by CH$_2$Cl$_2$ (10 mL), centrifuged, and the supernatant was decanted. The purple solid was subjected to three further cycles of suspension in CH$_2$Cl$_2$ (10 mL), centrifugation, and decantation to provide the 79 mg (75%) of the title compound as a purple solid (79 mg, 75%). $^1$H NMR (400 MHz, DMSO-d$_6$, δ): 10.35 (s, 1H), 8.92 (t, 1.8 Hz, 1H), 8.74 (d, 8.4 Hz, 2H), 8.25 (dt, J=8.4, 1.7 Hz, 1H), 8.09 (d, J=8.4, 2H), 7.94 (dt, J=8.4, 1.7 Hz, 1H), 7.64 (t, J=8.4 Hz, 1H), 2.83 (s, 4H), 2.81 (t, J=7.4 Hz, 2H) 2.53 (t, J=7.4 Hz, 2H), 1.97 (q, J=7.4 Hz, 2H).

Tetrazine-RGD Conjugate (18)

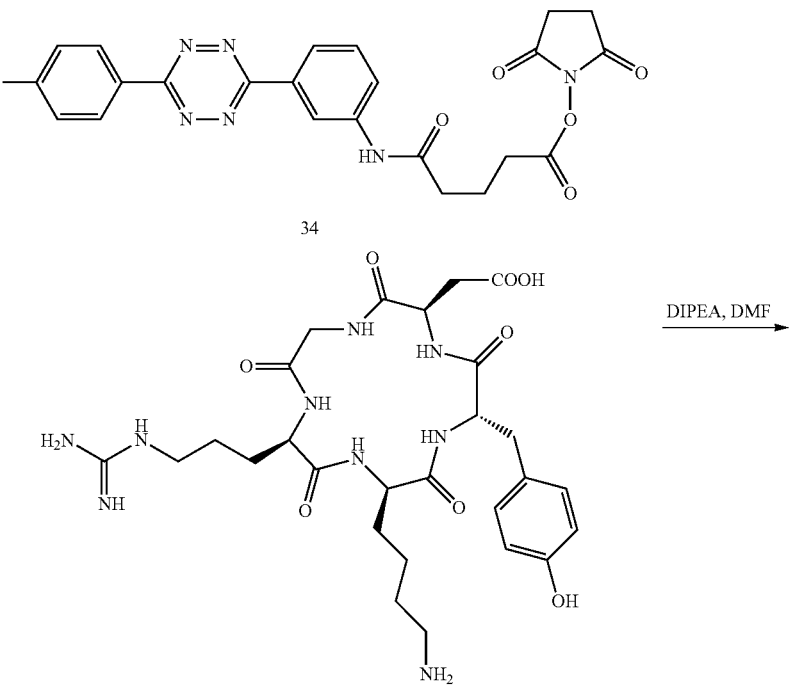

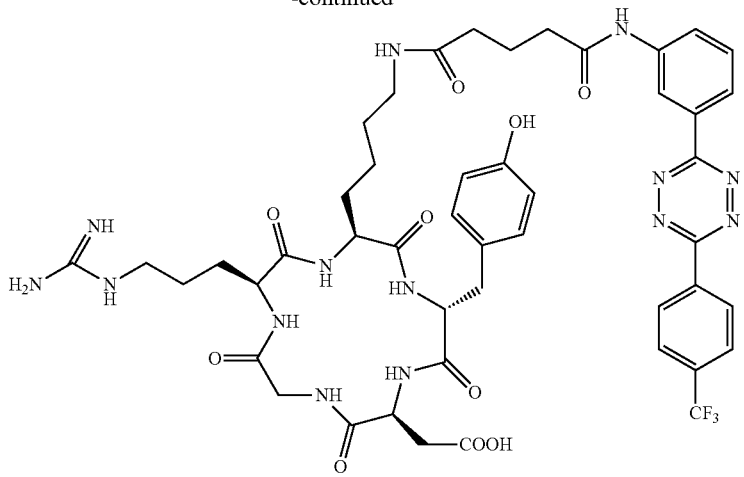

18

A dry 3 mL vial was charged with 34 (10.6 mg, 0.02 mmol) and 12 (6.2 mg, 0.01 mmol). The vial was capped by a screw cap with a Teflon septum, and the vial was swept with nitrogen. A solution of diisopropylethylamine (5.2 mg, 0.04 mmol) in DMF (110 µL) was added via syringe, followed by the addition of DMF (390 µL). The reaction mixture was allowed to stir for 18 h at room temperature. The mixture was centrifuged, and the residue was dissolved in 800 µL of DMSO and purified by reverse phase HPLC to provide 18 as a purple solid (2.2 mg, 11%). LCMS (m/z): [M−H]$^+$: calcd for $C_{47}H_{55}F_3N_{14}O_{10}{}^+$, 1032; found: 1033.

Tetrazine-RGD Conjugate (41)

Cyclic peptide c(RGDyC) (39) peptide which targets $\alpha_v\beta_3$-integrin on cell surfaces. A tetrazine conjugate 41 was prepared from c(RGDyC) (39) according to the following sequence.

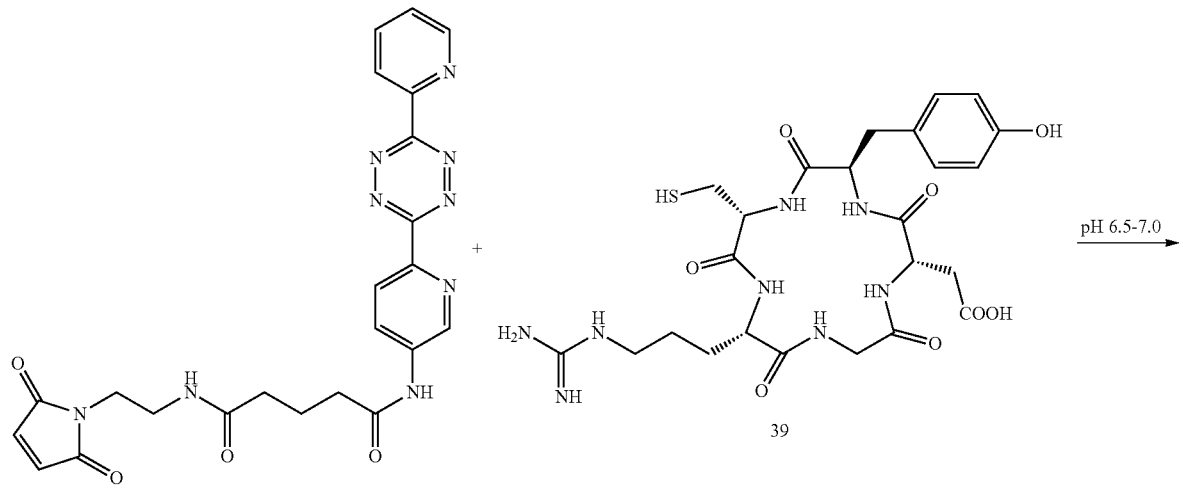

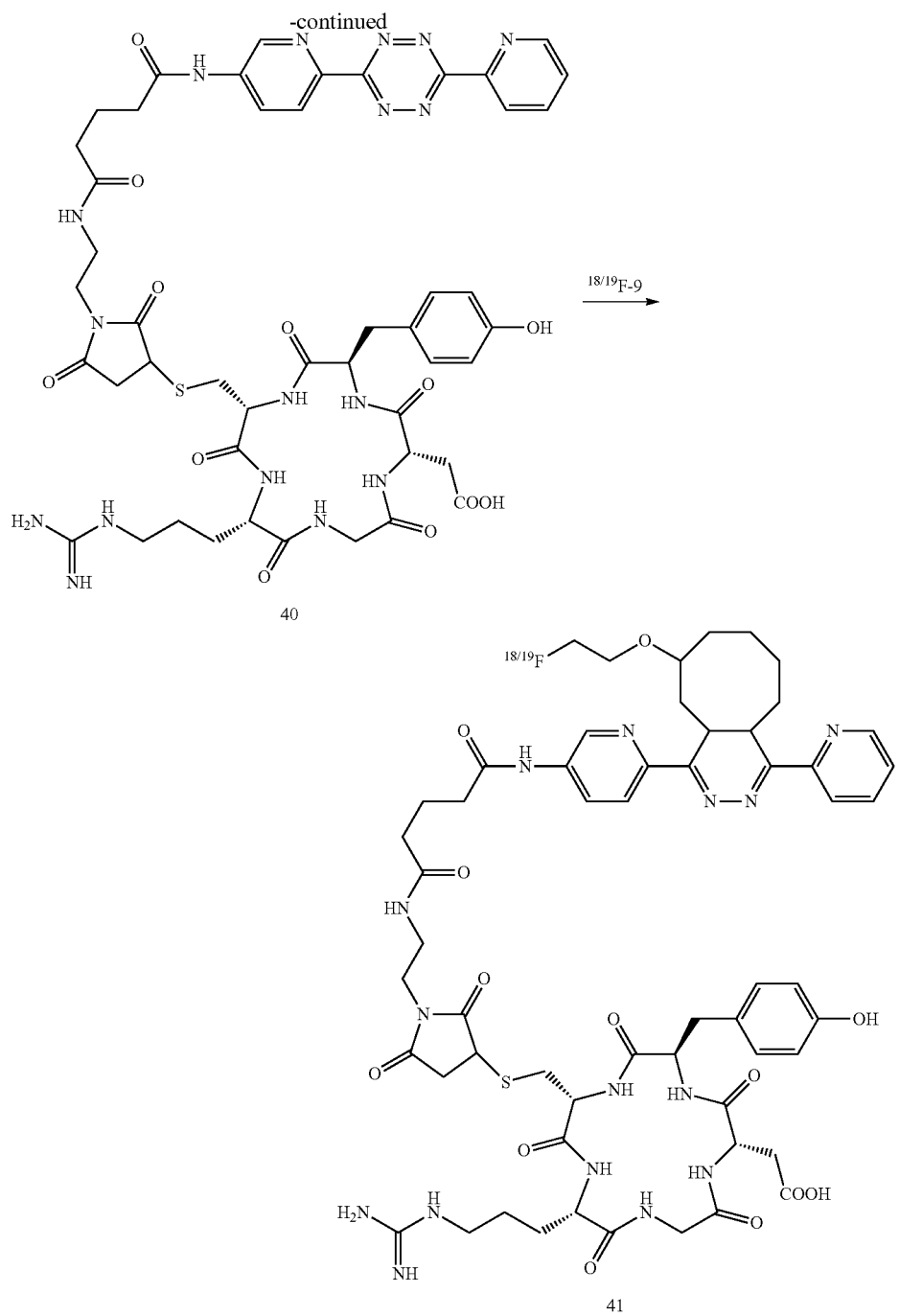

Conjugation of c(RGDyC) (39) and Tetrazine-Maleimide 24 to Form 40

The conjugation followed the method of Cai W, Zhang X, Wu Y, Chen X, employing a thiol-reactive 18F-labeling agent, N-[2-(4-18F-fluorobenzamido)ethyl]maleimide, and synthesis of RGD peptide-based tracer for PET imaging of alpha v beta 3 integrin expression. J Nucl Med. 2006; 47:1172-1180. Briefly, tetrazine-maleimide (200 μg, 0.41 μmol) in 100 μL dimethyl sulfoxide (DMSO) and 39 (200 μg, 0.33 μmol) (Peptides International of Louisville, Ky.) in 500 μL phosphate buffer (50 mM, pH 6.5-7.0) were mixed together at room temperature. After the mixture was stirred at room temperature for 5 h, the conjugate was purified by semipreparative HPLC. The collected fractions were combined and lyophilized to afford the final product as a white powder. Compound 40 was obtained in 85% yield.

Conjugation of VEGF and Tetrazine-Maleimide to Form 42

Briefly, tetrazine-maleimide 24 (200 μg, 0.41 μmol) in 100 μL DMSO and VEGF (100 μg, 5.5 nmol) in 500 μL phosphate buffer (50 mM, pH 6.5-7.0) were mixed together at room temperature. After the mixture was stirred at room temperature for 5 h, the conjugate was purified by size exclusion PD-10 column and concentrated by Centricon filter (Millipore, Bedford, Mass.), and the final concentration was determined based on UV absorbance at 280 nm using unconjugated VEGF of known concentrations as standard. The final concentration was adjusted to 50 μg/mL for use.

Synthesis of $^{19}$F-41

$^{19}$F-9 was synthesized according to Li Z, Cai H, Hassink M, Blackman M L, Brown R C, Conti P S, et al. Tetrazine-trans-cyclooctene ligation for the rapid construction of 18F labeled probes. Chem Commun (Camb). 2010; 46:8043-8045. 40 (100 μg, 92 nmol) in 100 μL DMSO and $^{19}$F-9 (200 μg, 0.33 μmol) in 100 μL DMSO were mixed together at room temperature. After the mixture was stirred at room temperature for 5 min, the conjugate was purified by semipreparative HPLC. The collected fractions were combined and lyophilized to afford the final product as a white powder. $^{19}$F-41 was obtained in 92% yield with 15.5 min retention time on analytical HPLC. MALDI-TOF-MS was m/z 1226.4 for [MH]$^+$ ($C_{57}H_{73}FN_{15}O_{13}S$, calculated molecular weight 1226.5).

Synthesis of $^{18}$F-41

$^{18}$F-9 was synthesized according to Li Z, Cai H, Hassink M, Blackman M L, Brown RC, Conti P S, et al. Tetrazine-trans-cyclooctene ligation for the rapid construction of 18F labeled probes. Chem Commun (Camb). 2010; 46:8043-8045. $^{18}$F-9 (148 MBq, 4 mCi) in about 50 μL ethanol was added to 40 (10 μg) in 50 μL DMSO followed by shaking for 5 min. The conjugate was purified by semipreparative HPLC. The collected fractions were combined and the solvent was removed by rotary evaporation under reduced pressure. $^{18}$F-41 was reconstituted in 1 mL PBS and passed through a 0.22 μm syringe filter for in vivo animal experiments.

Synthesis of $^{18}$F-43

$^{18}$F-9 (148 MBq, 4 mCi) in about 50 μL ethanol was added to the 42 (10 μg) in water followed by shaking for 5 min. The conjugate was purified by PD-10 column using 1×PBS as eluent. The collected fractions and passed through a 0.22 μm syringe filter for in vivo animal experiments.

Cell Culture

Human glioblastoma cell line U87MG cells were obtained from the American Type Culture Collection (Manassas, Va.) and were cultured in DMEM containing high glucose (GIBCO, Carlsbad, Calif.), which was supplemented with 10% fetal bovine serum (FBS) and 1% penicillin-streptomycin. The cells were expanded in tissue culture dishes and kept in a humidified atmosphere of 5% $CO_2$ at 37° C. The medium was changed every other day. A confluent monolayer was detached with 0.05% Trypsin-EDTA, 0.01M PBS (pH 7.4) and dissociated into a single-cell suspension for further cell culture.

MicroPET Imaging

Animal procedures were performed according to a protocol approved by the University of Southern California Institutional Animal Care and Use Committee. For static microPET scans, mice bearing U87MG xenografts were injected with 3.7 MBq (100 μCi) of $^{18}$F-41 via the tail vein (n=3 for each group). At 0.5, 1, and 2 h post injection (p.i.), the mice were anesthetized with isoflurane (5% for induction and 2% for maintenance in 100% $O_2$) using a knock-down box. With the help of a laser beam attached to the scanner, the mice were placed in the prone position and near the center of the field of view of the scanner. The 3-min static scans were then obtained. Images were reconstructed using a 2-dimensional ordered-subsets expectation maximization (OSEM) algorithm. No background correction was performed. Regions of interest (ROIs; 5 pixels for coronal and transaxial slices) were drawn over the tumor on decay-corrected whole-body coronal images. The maximum counts per pixel per minute were obtained from the ROI and converted to counts per milliliter per minute using a calibration constant. With the assumption of a tissue density of 1 g/mL, the ROIs were converted to counts per gram per min. Image ROI-derived % ID/g values were determined by dividing counts per gram per minute with injected dose. No attenuation correction was performed. Similarly, $^{18}$F-43 was injected into healthy nude mice for microPET study.

Chemistry and Radiochemistry

The conjugation of tetrazine-maleimide with 39 and VEGF proceeded smoothly in the phosphate buffer with pH 6.5-7.0. The nonradioactive cyclization reaction of 40 and $^{19}$F-9 was performed and the product was used for characterization and as a standard for $^{18}$F labeled product. Right after addition of $^{19}$F-9 to the solution of 40, the pink color of 40 disappeared, indicating completion of the reaction. The identity of the $^{19}$F-41 was confirmed by MALDI-TOF-MS. $^{19}$F-9 was produced using the protocol described in Li Z, Cai H, Hassink M, Blackman M L, Brown R C, Conti P S, et al. Tetrazine-trans-cyclooctene ligation for the rapid construction of 18F labeled probes. Chem Commun (Camb). 2010; 46:8043-8045. The radiolabeling yields for $^{18}$F-41 and $^{18}$F-43 showed almost quantitative capture of $^{18}$F-9. The radiopurity of $^{18}$F-41 was more than 95%, determined by radio HPLC. The specific activity of $^{18}$F-41 and $^{18}$F-43 were estimated to be about 3-6 Ci/μmol.

MicroPET Imaging

Figure 3:
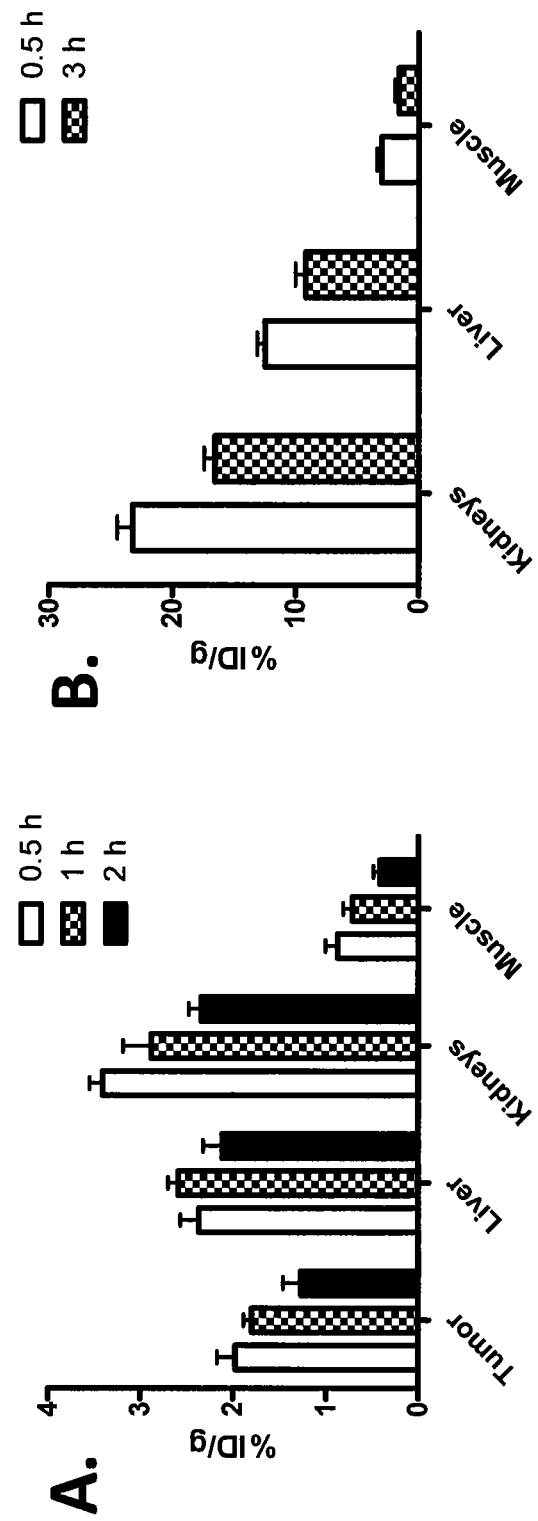
FIG. 3A shows tumor and major organ uptake of $^{18}$F-41.
FIG. 3B shows the biodistribution of $^{18}$F-43 in regions of interest in normal Sprague Dawley nude mice by microPET quantification.

Representative coronal microPET images of U87MG tumor-bearing mice (n=3/group) were obtained at different times after intravenous injection of about 3.7 MBq (100 μCi) of $^{18}$F-41. The tumors after injection of the radiotracers were all clearly visible with good contrast to contralateral background at all time points measured. The mice showed high abdominal activity accumulation. Prominent uptake of $^{18}$F-41 was observed in the kidneys and urinary bladder at early time points, indicating that this radiotracer is mainly excreted through the renal system. Quantification of tumor and major organ activity accumulation in the microPET scans was achieved by measuring regions of interest (ROIs) encompassing the entire organ on the coronal images. Tumor and major organ uptake of $^{18}$F-41 is depicted in FIG. 3A. The tumor uptake of $^{18}$F-41 in U87MG tumor was 1.98±0.33, 1.80±0.15, and 1.27±0.33% ID/g at 0.5, 1, and 2 h p.i., respectively. The uptake of the $^{18}$F-41 decreased rapidly with time in the muscle, affording better image contrast at later time points after injection (2 h).

The biodistribution of $^{18}$F-43 was evaluated in normal Sprague Dawley nude mice. Representative coronal microPET images at 0.5 and 3 h post injection of about 3.7 MBq (100 μCi) $^{18}$F-43 were obtained. The activity was mainly accumulated in the liver and kidney. MicroPET quantification by measuring the ROI is shown in FIG. 3B. The kidney uptakes of $^{18}$F-43 were 23.20±2.15 and 16.51±1.52% ID/g at 30 min and 180 min post injection respectively. Low muscle uptakes were observed (2.98±0.66 and 1.59±0.57% ID/g at 0.5 and 3 h post injection).

Diaminotetrazine (21)

Diaminotetrazine (21) was prepared as follows.

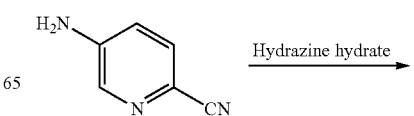

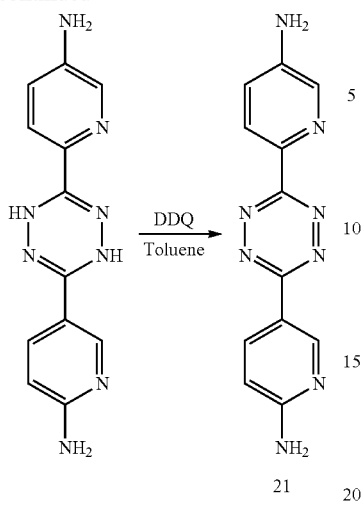

¹H NMR (400 MHz, DMSO-d₆, δ) 21: 8.27 (d, J=8.8 Hz, 2H), 8.20 (d, J=2.3 Hz, 2H), 7.10 (dd, J=8.8, 2.3 Hz, 2H), 6.24 (s, 4H).

N¹-(2-(2,5-dioxo-2,5-dihydro-1H-pyrrol-1-yl)ethyl)-N⁵-(6-(6-(pyridin-2-yl)-1,2,4,5-tetrazin-3-yl)pyridin-3-yl)glutaramide (24)

Compound 24 was prepared according to the following sequence.

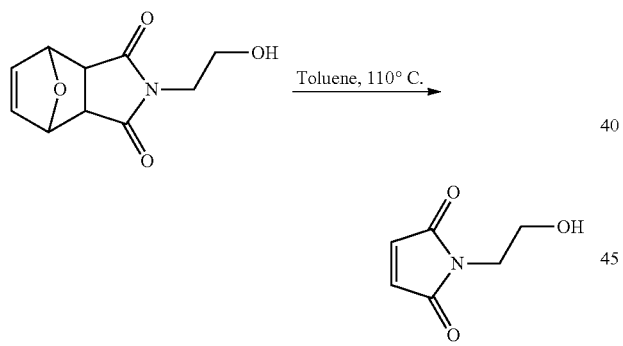

To a flame dried flask 1.78 g (8.52 mmol) of 4-(2-hydroxyethyl)-10-oxa-4-aza-tricyclo[5.2.1.02,6]-dec-8-ene-3,5-dione (Willson, C. G. *Macromolecules* 2008, 41, 719) was added. The flask was equipped with a condenser. The flask was then evacuated and refilled with nitrogen. Toluene (36 mL) was added. The reaction flask was heated to 110° C. and stirred and sparged with nitrogen for 5 hr. The flask was then cooled to 0° C. The mixture was filtered in a Buchner funnel and washed with diethyl ether (20 mL). The collected solid was then sublimed and collected to yield 28% (0.339 g, 2.40 mmol) of 1-(2-hydroxyethyl)-1H-pyrrole-2,5-dione.

¹H NMR (400 MHz, CD3Cl) 6.74 (s, 2H), 3.82-3.77 (m, 2H), 3.74-3.70 (m, 2H), 2.03 (brs, 1H)

To a flame dried round bottom flask 0.5 g (3.6 mmol) of 1-(2-hydroxyethyl)-1H-pyrrole-2,5-dione and 0.7 g (4.0 mmol) of methanesulfonic anhydride was added. The flask was evacuated and refilled with nitrogen. The flask was heated to 105° C. and stirred for 3.5 hr. The reaction was cooled to room temperature and dissolved in ethyl acetate (5 mL). The solution was taken up into a separatory funnel and washed four times with a saturated solution of sodium carbonate (40 mL). The aqueous layers were collected and washed with ethyl acetate (50 mL). The organic layers were combined and dried with MgSO₄ and concentrated in vacuo. The product was recrystallized from t-butyl methyl ether to yield 43% (0.347 g, 1.58 mmol) of 2-(2,5-dioxo-2,5-dihydro-1H-pyrrol-1-yl)ethyl methanesulfonate.

¹H NMR (400 MHz, CD₃Cl) 6.78 (s, 2H), 4.41 (t, J=5.23, 2H), 3.90 (t, J=5.23, 2H), 3.04 (s, 3H)

N¹-(2-(2,5-dioxo-2,5-dihydro-1H-pyrrol-1-yl)ethyl)-N⁵-(6-(6-(pyridin-2-yl)-1,2,4,5-tetrazin-3-yl)pyridin-3-yl)glutaramide (24)

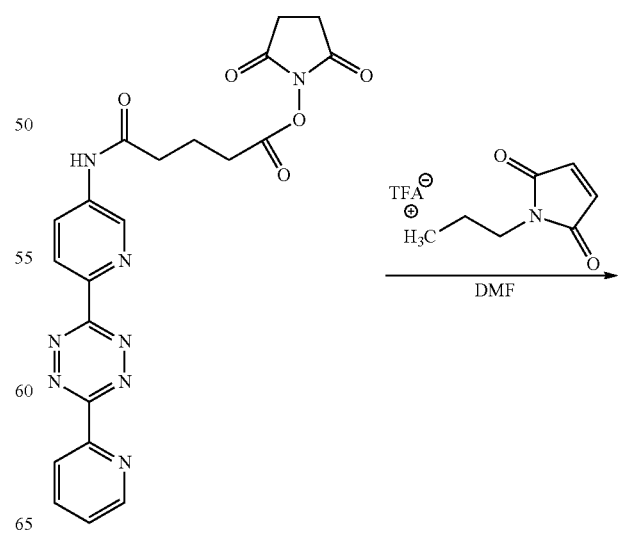

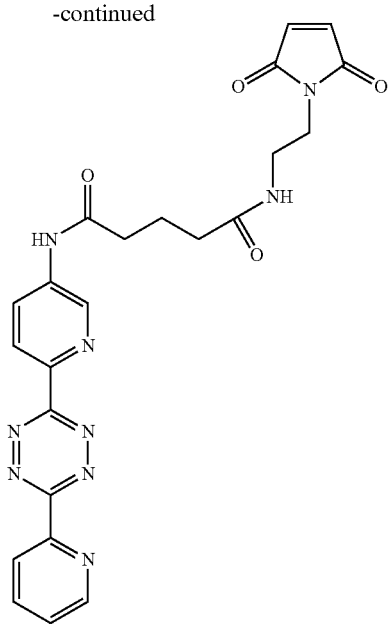

24

To a flame dried flask was added 0.03 g (0.065 mmol, 1 eq.) of 2,5-dioxopyrrolidin-1-yl 5-oxo-5-((6-(6-(pyridin-2-yl)-1,2,4,5-tetrazin-3-yl)pyridin-3-yl)amino)pentanoate (13), followed by 0.02 g (0.078 mmol, 1.2 eq.) of 2-(2,5-dioxo-2,5-dihydro-1H-pyrrol-1-yl)ethanaminium trifluoroacetate. The flask was evacuated and then refilled with nitrogen. DMF (1 ml) was added and the mixture was stirred. Diisopropylethyl amine (0.032 ml, 0.195 mmol, 3 eq.) was added dropwise to the mixture. The reaction mixture was stirred for 24 hours at room temperature. The reaction was condensed in vacuo and then loaded onto a silica gel column using the minimum amount of MeOH required along with $CH_2Cl_2$. The column was then run using a gradient of 0-10% MeOH in $CH_2Cl_2$ to yield 48% (0.015 g, 0.031 mmol) of $N^1$-(2-(2,5-dioxo-2,5-dihydro-1H-pyrrol-1-yl)ethyl)-$N^5$-(6-(6-(pyridin-2-yl)-1,2,4,5-tetrazin-3-yl)pyridin-3-yl)glutaramide.

$^1$H NMR (400 MHz, $CD_3OD$) δ 9.06 (d, J=2.3 Hz, 1H), 8.92-8.88 (m, 1H), 8.82-8.75 (m, 2H), 8.51 (dd, J=8.8, 2.6 Hz, 1H), 8.19 (dt, J=1.7, 7.8 Hz, 1H), 7.80-7.69 (m, 1H), 6.84 (s, 2H), 5.51 (s, 1H), 4.60 (s, 2H), 3.72-3.56 (m, 2H), 3.42-3.36 (m, 2H), 2.68 (s, 1H), 2.53 (t, J=7.3 Hz, 2H), 2.27 (t, J=7.4 Hz, 2H), 2.08-1.90 (m, 2H).

Although the invention is illustrated and described herein with reference to specific embodiments, the invention is not intended to be limited to the details shown. Rather, various modifications may be made in the details within the scope and range of equivalents of the claims without departing from the invention.

What is claimed is:

1. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct.

2. The Diels-Alder adduct of claim 1, wherein the tetrazine residue of the Diels-Alder adduct is covalently bound to a biomolecule.

3. The Diels-Alder adduct of claim 2, wherein the biomolecule is in an animal or human.

4. The Diels-Alder adduct of claim 2, wherein the tetrazine residue is a residue formed by reaction of the biomolecule with a compound according to structure 13

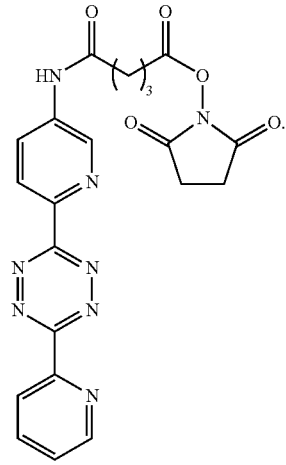

13

5. The Diels-Alder adduct of claim 2, wherein the tetrazine residue is a residue formed by reaction of the biomolecule with a compound according to structure 24

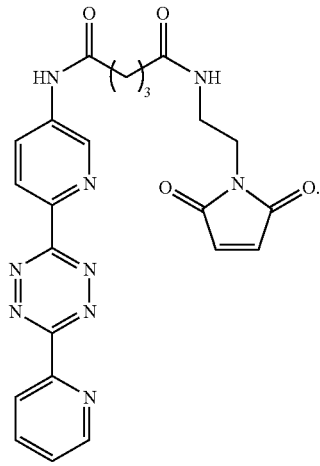

24

6. The Diels-Alder adduct of claim 2, wherein the radionuclide is $^{18}$F.

7. The Diels-Alder adduct of claim 6, wherein the trans-cyclooctene residue is a residue of the compound according to structure 9

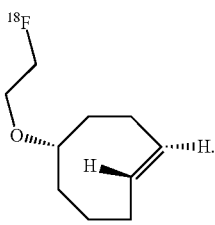

9

8. The Diels-Alder adduct of claim 6, wherein the trans-cyclooctene residue is a residue of the compound according to structure 17

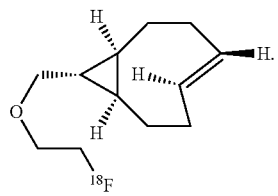

17

9. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct, wherein the tetrazine residue is a residue of the compound according to structure 5

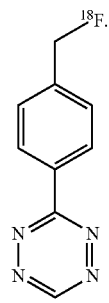

5

10. The compound according to structure 9

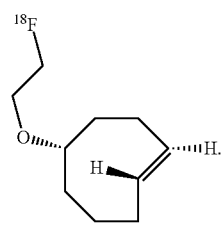

9

11. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct, wherein the trans-cyclooctene residue is a residue of the compound according to structure 17

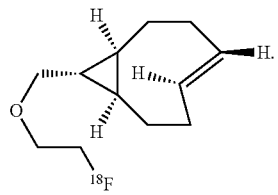

17

12. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct, wherein the tetrazine residue is a residue of the compound according to structure 13

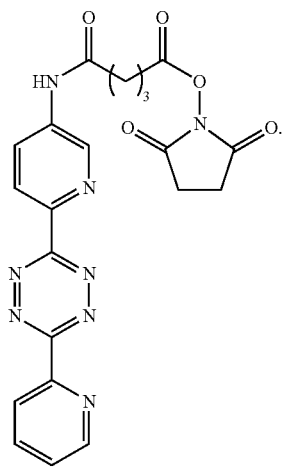

13

13. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct, wherein the tetrazine residue is a residue of the compound according to structure 24

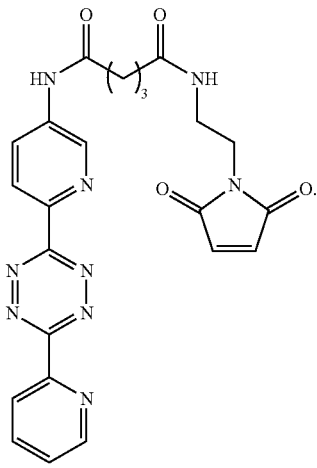

24

14. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct, wherein the tetrazine residue is a residue of the compound according to structure 14

14

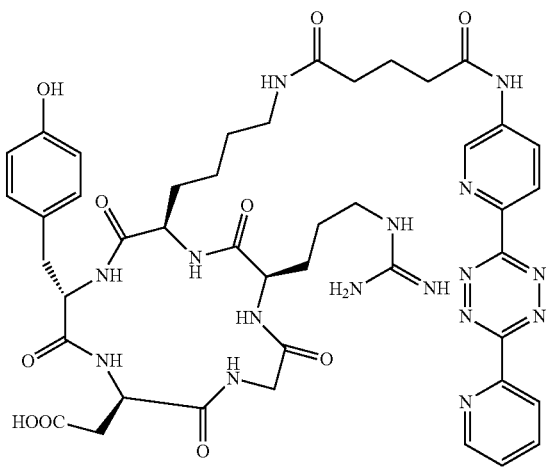

15. The compound according to structure 15

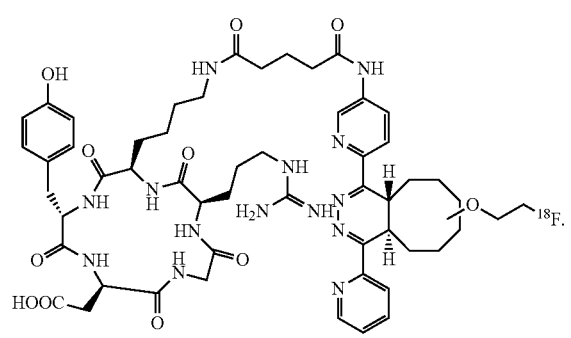

16. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct, wherein the tetrazine residue is a residue of the compound according to structure 18

18

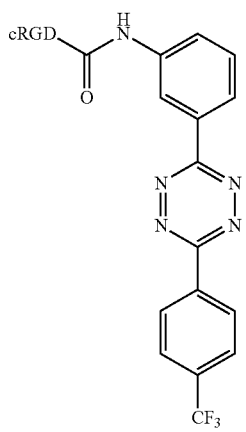

17. The compound according to structure 19

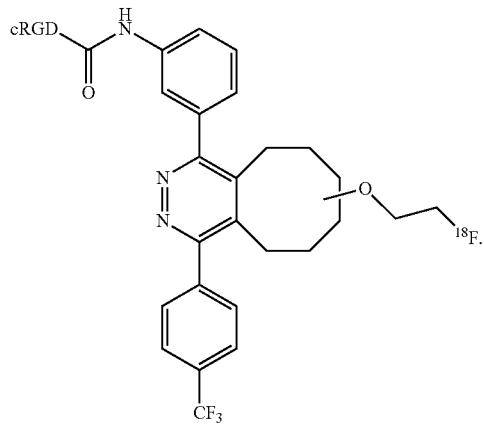

18. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct, wherein the adduct is the compound according to structure 20

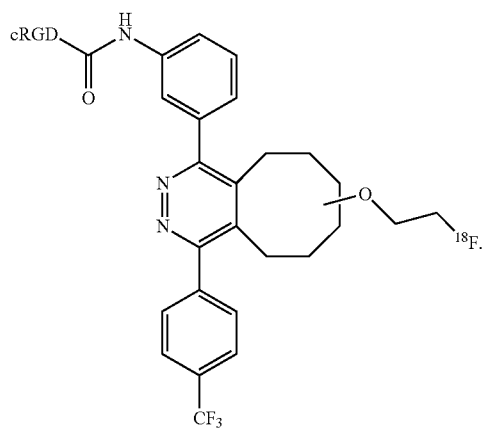

19. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct, wherein the tetrazine residue is a residue of the compound according to structure 22

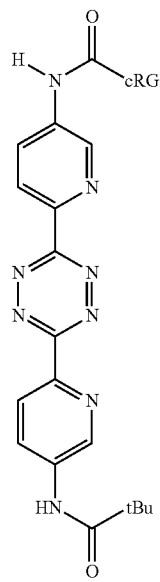
22
20. A Diels-Alder adduct of a trans-cyclooctene with a tetrazine, wherein the adduct bears a substituent labeled with a radionuclide, wherein the substituent is a substituent on the trans-cyclooctene residue of the Diels-Alder adduct, wherein the tetrazine residue is a residue of the compound according to structure 29
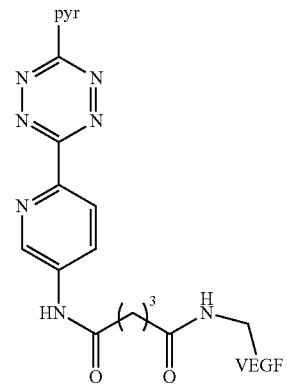
29
21. The compound accordina to structure 31
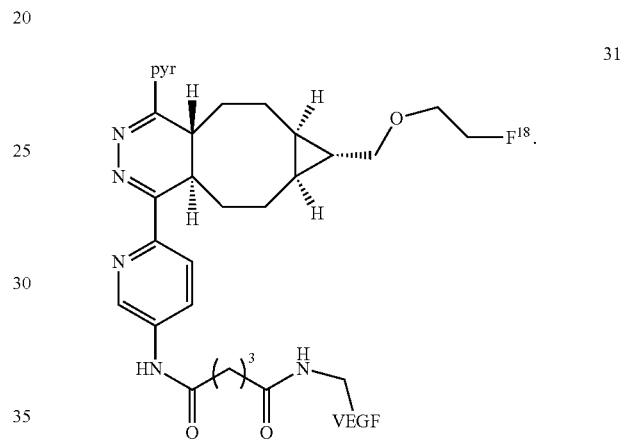
31
* * * * *